US009725487B2

(12) United States Patent
Garry et al.

(10) Patent No.: US 9,725,487 B2
(45) Date of Patent: Aug. 8, 2017

(54) COMPOSITIONS AND METHODS FOR MEASLES VIRUS INHIBITION

(71) Applicant: The Administrators of the Tulane Educational Fund, New Orleans, LA (US)

(72) Inventors: Robert F. Garry, New Orleans, LA (US); Russell B. Wilson, Mandeville, LA (US)

(73) Assignees: The Administrators of the Tulane Educational Fund, New Orleans, LA (US); Autoimmune Technologies, LLC, New Orleans, LA (US)

( * ) Notice: Subject to any disclaimer, the term of this patent is extended or adjusted under 35 U.S.C. 154(b) by 0 days.

(21) Appl. No.: 14/711,364

(22) Filed: May 13, 2015

(65) Prior Publication Data

US 2015/0239940 A1    Aug. 27, 2015

Related U.S. Application Data

(60) Division of application No. 13/962,524, filed on Aug. 8, 2013, now Pat. No. 9,056,900, which is a division of application No. 13/482,388, filed on May 29, 2012, now Pat. No. 8,598,116, which is a division of application No. 12/378,558, filed on Feb. 17, 2009, now abandoned, which is a continuation of application No. 10/578,013, filed as application No. PCT/US2004/036578 on Nov. 3, 2004, now Pat. No. 7,491,793.

(60) Provisional application No. 60/517,181, filed on Nov. 4, 2003.

(51) Int. Cl.
| | |
|---|---|
| *C07K 14/005* | (2006.01) |
| *A61K 38/04* | (2006.01) |
| *A61K 38/16* | (2006.01) |
| *C07K 7/00* | (2006.01) |
| *C07K 7/08* | (2006.01) |
| *C12Q 1/18* | (2006.01) |
| *C07K 7/06* | (2006.01) |
| *G01N 33/569* | (2006.01) |
| *C12N 7/00* | (2006.01) |
| *A61K 38/00* | (2006.01) |

(52) U.S. Cl.
CPC ............ *C07K 14/005* (2013.01); *A61K 38/04* (2013.01); *A61K 38/162* (2013.01); *C07K 7/00* (2013.01); *C07K 7/08* (2013.01); *C12N 7/00* (2013.01); *C12Q 1/18* (2013.01); *G01N 33/56988* (2013.01); *A61K 38/00* (2013.01); *C07K 7/06* (2013.01); *C12N 2760/10022* (2013.01); *C12N 2760/14122* (2013.01); *C12N 2760/18422* (2013.01); *C12N 2760/18433* (2013.01); *C12N 2770/20022* (2013.01)

(58) Field of Classification Search
None
See application file for complete search history.

(56) References Cited

U.S. PATENT DOCUMENTS

| | | | |
|---|---|---|---|
| 5,464,933 A | 11/1995 | Bolognesi et al. |
| 5,567,805 A | 10/1996 | Henderson et al. |
| 5,747,239 A | 5/1998 | Wang et al. |
| 6,037,348 A | 3/2000 | Colacino et al. |
| 7,420,028 B2 | 9/2008 | Bogoch et al. |
| 7,442,761 B2 | 10/2008 | Bogoch et al. |
| 7,452,963 B2 | 11/2008 | Bogoch et al. |
| 7,674,880 B2 | 3/2010 | Bogoch et al. |
| 7,705,129 B2 | 4/2010 | Bogoch et al. |
| 7,758,863 B2 | 7/2010 | Bogoch et al. |
| 7,763,705 B2 | 7/2010 | Bogoch et al. |
| 7,774,144 B2 | 8/2010 | Bogoch et al. |
| 7,894,999 B2 | 2/2011 | Bogoch et al. |
| 2003/0180328 A1 | 9/2003 | Bogoch et al. |
| 2007/0026009 A1 | 2/2007 | Bogoch et al. |

FOREIGN PATENT DOCUMENTS

| | | |
|---|---|---|
| WO | 8808429 A1 | 11/1988 |
| WO | 9417826 A1 | 8/1994 |
| WO | 0032228 A2 | 6/2000 |
| WO | 0151673 A1 | 7/2001 |
| WO | 0159457 A2 | 8/2001 |
| WO | 0224734 A2 | 3/2002 |
| WO | 2005010034 A1 | 2/2005 |
| WO | 2005016238 A2 | 2/2005 |
| WO | 2005044992 A2 | 5/2005 |

OTHER PUBLICATIONS

Cameron, T. O., et al., Examination of the Highly Diverse CD4+ T-Cell Repertoire Directed Against an Influenza Peptide: A Step Towards TCR Proteomics, Immunogenetics, vol. 54, 611-620 (2002).
Gelder, C.M., et al., Human CD4+ T-Cell Recognition of Influenza A Virus Hemagglutinin After Subunit Vaccination, Journal of Virology, vol. 70 (7), 4787-4790 (1996).
Gelder, C., et al., Six Unrelated HLA-DR-Matched Adults Recognize Identical CD4+ T Cell Epitopes from Influenza A Hemagglutinin That Are Not Simply Peptides With High HLA-DR Binding Affinities, International Immunology, vol. 10 (2), 211-222 (1998).
Gelder. C., et al., Associations Between Human Leukocyte Antigens and Nonresponsiveness to Influenza Vaccine, Journal of Infectious Diseases, vol. 185, 114-117 (2002).
Janeway, C.A., Jr. et al., Synthetic Peptides of Protective Antigens Can Elicit Protective Immunity, Immuno Biology 5, The Immune System in Health and Disease, 586-587 (2001).

(Continued)

*Primary Examiner* — Nicole Kinsey White
(74) *Attorney, Agent, or Firm* — Olson & Cepuritis, Ltd.

(57) ABSTRACT

The present invention provides compositions and methods for treating a measles virus infection. A pharmaceutical composition comprises a polypeptide in a biocompatible pharmaceutical carrier, in which the polypeptide consists of at least a portion of SEQ ID NO: 5 or SEQ ID NO: 6. A method embodiment comprises administering the polypeptide (preferably in a biocompatible pharmaceutical carrier) to a subject suffering from a measles infection.

13 Claims, 9 Drawing Sheets

(56) References Cited

OTHER PUBLICATIONS

Levy, D. N., et al., Synthetic Peptide-Based Vaccines and Antiviral Agents Including HIV/AIDS as a Model System, Biologically Active Peptides: Design, Synthesis, and Utilization, vol. 1, 219-266 (1993).

Lina, B., et al., A TritonX-100-Split Virion Influenza Vaccine is Safe and Fulfills the Committee for Proprietary Medicinal Products (CPMP) Recommendations for the European Community for Immunogenicity, in Children, Adults and the Elderly, Biologicals, vol. 28, 95-103 (2000).

Lu, X., et al., A Mouse Model for the Evaluation of Pathogenesis and Immunity to Influenza A (H5N1) Viruses Isolated from Humans, Journal of Virology, vol. 73 (7), 5903-5911 (1999).

Powers, D. C., et al., Humoral and Cellular Immune Responses Following Vaccination with Purified Recombinant Hemagglutinin from Influenza a (H3N2) Virus, the Journal of Infectious Diseases, vol. 175, 342-351 (1997).

Steigerwald-Mullen, P., et al., Type 2 Cytokines Predominate in the Human CD4+T-Lymphocyte Response to Epstein-Barr Virus Nuclear Antigen 1, Journal of Virology, vol. 74 (15), 6748-6759 (2000).

Williams, O. M., et al., Analysis of CD4+ T-Cell Responses to Human Papillomavirus (HPV) Type 11 L1 in Healthy Adults Reveals a High Degree of Responsiveness and Cross-Reactivity with Other HPV Types, Journal of Virology, vol. 76 (15), 7418-7429 (2002).

Gelder, C., et al., Human CD4+ T-Cell Repertoire of Responses to Influenza A Virus Hemagglutinin After Recent Natural Infection, Journal of Virology, vol. 69, p. 7497-7506 (1995).

Russel, R.J., et al., Structure of Influenza Hemagglutinin in Complex With an Inhibitor of Membrane Fusion, PNAS, vol. 105 (46), 17736-17741 (2008).

Fass, D., et al., Dissection of a Retrovirus Envelope Protein Reveals Structural Similarity to Influenza Hemagglutinin, Current Biology, vol. 5 (12), 1377-1383 (1995).

Carr, C.M, et al., A Spring-Loaded Mechanism for the Conformational Change of Influenza Hemagglutinin, Cell, vol. 73, pp. 823-832 (1993).

Clegg, J.C.S., et al., Nucleotide Sequence of the S RNA of Lassa Virus . . . of Arenavirus Gene Products, Virus Research, vol. 18, 151-164 (1990).

Chan, D.C., et al., Evidence that a Prominent Cavity in the Coiled Coil of HIV . . . Attractive Drug Target, Proc. Natl. Acad. Sci., vol. 95, 15613-15617 (1998).

Atabani, S.F., et al., Identification of an Immunodominant Neutralizing . . . Human Sera From Acute Infection; Journal of Virology, 7240-7245 (1997).

Samuel, O., et al., Participation of Two Fusion Peptides in Measles Virus-Induced Membrane Fusion . . . With Other Paramyxoviruses, Biochemistry 40, 1340-1349 (2001).

Kliger, Y. et al., Cloaked Similarity Between HIV-1 and SARS-CoV Suggests an Anti-SARS Strategy, BMC Microbiology, vol. 3, Research Article (2003).

Huang, J., et al., A Novel Dry Powder Influenza Vaccine and Intranasal Delivery Technology: Induction of Systemic and Mucosal Immune Responses in Rats, Vaccine 23, 794-801 (2004).

Yoshimoto, J., et al., Development of Anti-Influenza Drugs: II. Improvement of Oral and Intranasal Absorption and the Anti-Influenza Activity of Stachyflin Derivatives, J. Pharm. Pharmacol. 52, 1247-1255 (2000).

Roberts, M.J. et al., Chemistry for Peptide and Protein PEGylation, Advanced Drug Delivery Reviews 54, 459-476 (2002).

Ayyoub, M. et al., Activation of Human Melanoma Reactive CD8+ T Cells by Vaccination with an Immunogenic Peptide Analog Derived from Melan-A/Melanoma Antigen . . . Clinical Cancer Research, vol. 9, 669-677 (2003).

Gherardi, M.M. et al., Prime-Boost Immunization Schedules Based on Influenza Virus and Vaccinia Virus Vectors Potentiate Cellular Immune Responses Against Human Immunodeficiency Virus Env Protein Systemically and in the Genitorectal Draining Lymph Nodes, Journal of Virology, vol. 77 (12) 7048-7057 (2003).

Aurora, J., Development of Nasal Delivery Systems: A Review, vol. 2 (7), (2002).

Krasko, A.G. et al., Lassa Virus Glycoproteins: Antigenic and Immunogenic Properties of Synthetic Peptides to GP1, Archives of Virology, vol. 115, 133-137 (1990).

Liu, S., et al., Interaction Between Heptad Repeat 1 and 2 Regions in Spike Protein of SARS-Associated Coronavirus: Implications for Virus Fusogenic Mechanism and Identification of Fusion Inhibitors, Mechanisms of Disease, The Lancet, vol. 363, 938-947 (2004).

Ren, Y. et al., A Strategy for Searching Antigenic Regions in the SARS-CoV Spike Protein, Geno., Prot. & Bioinfo, vol. 1 (3), 207-215 (2003).

Xiao, X. et al., The SARS-CoV S Glycoprotein: Expression and Functional Characterization, Biochemical and Biophysical Research Communications, vol. 312, 1159-1164 (2003).

Lassa virus GP2
Figure 2

SARS CoV S
Figure 3

Ebola virus GP2
Figure 4 influenza virus HA2
Figure 5 measles virus F1
Figure 6

HIV-1 TM

Figure 9

SEQUENCE LISTING

```
<160> NUMBER OF SEQ ID NOS: 31

<210> SEQ ID NO 1
<211> LENGTH: 39
<212> TYPE: PRT
<213> ORGANISM: Artificial Sequence
<220> FEATURE:
<223> OTHER INFORMATION: Synthetic peptide

<400> SEQUENCE: 1

Leu Ile Met Lys Asn His Leu Arg Asp Ile Met Gly Ile Pro Tyr Cys
1               5                   10                  15

Asn Tyr Ser Arg Tyr Trp Tyr Leu Asn His Thr Ser Thr Gly Lys Thr
            20                  25                  30

Leu Pro Arg Cys Trp Leu Ile
        35

<210> SEQ ID NO 2
<211> LENGTH: 100
<212> TYPE: PRT
<213> ORGANISM: Artificial Sequence
<220> FEATURE:
<223> OTHER INFORMATION: Synthetic peptide

<400> SEQUENCE: 2

Leu Ile Arg Ala Ala Glu Ile Arg Ala Ser Ala Asn Leu Ala Ala Thr
1               5                   10                  15

Lys Met Ser Glu Cys Val Leu Gly Gln Ser Lys Arg Val Asp Phe Cys
            20                  25                  30

Gly Lys Gly Tyr His Leu Met Ser Phe Pro Gln Ala Ala Pro His Gly
        35                  40                  45

Val Val Phe Leu His Val Thr Tyr Val Pro Ser Gln Glu Arg Asn Phe
    50                  55                  60

Thr Thr Ala Pro Ala Ile Cys His Glu Gly Lys Ala Tyr Phe Pro Arg
65                  70                  75                  80

Glu Gly Val Phe Val Phe Asn Gly Thr Ser Trp Phe Ile Thr Gln Arg
```

Asn Phe Phe Ser
            100

<210> SEQ ID NO 3
<211> LENGTH: 32
<212> TYPE: PRT
<213> ORGANISM: Artificial Sequence
<220> FEATURE:
<223> OTHER INFORMATION: Synthetic peptide

<400> SEQUENCE: 3

Leu Arg Thr Phe Ser Ile Leu Asn Arg Lys Ala Ile Asp Phe Leu Leu
1               5                   10                  15

Gln Arg Trp Gly Gly Thr Cys His Ile Leu Gly Pro Asp Cys Cys Ile
            20                  25                  30

<210> SEQ ID NO 4
<211> LENGTH: 43
<212> TYPE: PRT
<213> ORGANISM: Artificial Sequence
<220> FEATURE:
<223> OTHER INFORMATION: Synthetic peptide

<400> SEQUENCE: 4

Ile Gln Asp Leu Glu Lys Tyr Val Glu Asp Thr Lys Ile Asp Leu Trp
1               5                   10                  15

Ser Tyr Asn Ala Glu Leu Leu Val Ala Leu Glu Asn Gln His Thr Ile
            20                  25                  30

Asp Leu Thr Asp Ser Glu Met Asn Lys Leu Phe
            35                  40

<210> SEQ ID NO 5
<211> LENGTH: 17
<212> TYPE: PRT
<213> ORGANISM: Artificial Sequence
<220> FEATURE:
<223> OTHER INFORMATION: Synthetic peptide

<400> SEQUENCE: 5

Leu Gly Leu Lys Leu Leu Arg Tyr Tyr Thr Glu Ile Leu Ser Leu Phe
1               5                   10                  15

Gly

<210> SEQ ID NO 6
<211> LENGTH: 94
<212> TYPE: PRT
<213> ORGANISM: Artificial Sequence
<220> FEATURE:
<223> OTHER INFORMATION: Synthetic peptide

<400> SEQUENCE: 6

Trp Tyr Thr Thr Val Pro Lys Tyr Val Ala Thr Gln Gly Tyr Leu Ile
1               5                   10                  15

Ser Asn Phe Asp Glu Ser Ser Cys Thr Phe Met Pro Glu Gly Thr Val
            20                  25                  30

Cys Ser Gln Asn Ala Leu Tyr Pro Met Ser Pro Leu Leu Gln Glu Cys
            35                  40                  45

Leu Arg Gly Ser Thr Lys Ser Cys Ala Arg Thr Leu Val Ser Gly Ser
            50                  55                  60

Phe Gly Asn Arg Phe Ile Leu Ser Gln Gly Asn Leu Ile Ala Asn Cys
65                  70                  75                  80

```
Ala Ser Ile Leu Cys Lys Cys Tyr Thr Thr Gly Thr Ile Ile
                85                  90
```

```
<210> SEQ ID NO 7
<211> LENGTH: 57
<212> TYPE: PRT
<213> ORGANISM: Artificial Sequence
<220> FEATURE:
<223> OTHER INFORMATION: Synthetic peptide

<400> SEQUENCE: 7

Leu Gln Ala Arg Ile Leu Ala Val Glu Arg Tyr Leu Lys Asp Gln Gln
1               5                   10                  15

Leu Leu Gly Ile Trp Gly Cys Ser Gly Lys Leu Ile Cys Thr Thr Ala
            20                  25                  30

Val Pro Trp Asn Ala Ser Trp Ser Asn Lys Ser Leu Glu Gln Ile Trp
        35                  40                  45

Asn His Thr Thr Trp Met Glu Trp Asp
    50                  55
```

```
<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Ile Leu Asn Arg Lys Ala Ile Asp Phe
1               5
```

```
<210> SEQ ID NO 9
<211> LENGTH: 8
<212> TYPE: PRT
<213> ORGANISM: Artificial Sequence
<220> FEATURE:
<223> OTHER INFORMATION: Synthetic peptide

<400> SEQUENCE: 9

Cys His Ile Leu Gly Pro Asp Cys
1               5
```

```
<210> SEQ ID NO 10
<211> LENGTH: 19
<212> TYPE: PRT
<213> ORGANISM: Artificial Sequence
<220> FEATURE:
<223> OTHER INFORMATION: Synthetic peptide

<400> SEQUENCE: 10

Phe Leu Leu Gln Arg Trp Gly Gly Thr Cys His Ile Leu Gly Pro Asp
1               5                   10                  15

Cys Cys Ile
```

```
<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

Leu Lys Leu Leu Arg Tyr Tyr Thr Glu
1               5
```

```
<210> SEQ ID NO 12
<211> LENGTH: 10
<212> TYPE: PRT
<213> ORGANISM: Artificial Sequence
<220> FEATURE:
<223> OTHER INFORMATION: Synthetic peptide

<400> SEQUENCE: 12

Cys Thr Phe Met Pro Glu Gly Thr Val Cys
1               5                   10

<210> SEQ ID NO 13
<211> LENGTH: 19
<212> TYPE: PRT
<213> ORGANISM: Artificial Sequence
<220> FEATURE:
<223> OTHER INFORMATION: Synthetic peptide

<400> SEQUENCE: 13

Trp Tyr Thr Thr Val Pro Lys Tyr Val Ala Thr Gln Gly Tyr Leu Ile
1               5                   10                  15

Ser Asn Phe

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

Cys Leu Arg Gly Ser Thr Lys Ser Cys
1               5

<210> SEQ ID NO 15
<211> LENGTH: 36
<212> TYPE: PRT
<213> ORGANISM: Artificial Sequence
<220> FEATURE:
<223> OTHER INFORMATION: Synthetic peptide

<400> SEQUENCE: 15

Thr Leu Val Ser Gly Ser Phe Gly Asn Arg Phe Ile Leu Ser Gln Gly
1               5                   10                  15

Asn Leu Ile Ala Asn Cys Ala Ser Ile Leu Cys Lys Cys Tyr Thr Thr
                20                  25                  30

Gly Thr Ile Ile
            35

<210> SEQ ID NO 16
<211> LENGTH: 234
<212> TYPE: PRT
<213> ORGANISM: LASSA VIRUS

<400> SEQUENCE: 16

Leu Leu Gly Thr Phe Thr Trp Thr Leu Ser Asp Ser Glu Gly Asn Glu
1               5                   10                  15

Thr Pro Gly Gly Tyr Cys Leu Thr Arg Trp Met Leu Ile Glu Ala Glu
                20                  25                  30

Leu Lys Cys Phe Gly Asn Thr Ala Val Ala Lys Cys Asn Glu Lys His
            35                  40                  45

Asp Glu Glu Phe Cys Asp Met Leu Arg Leu Phe Asp Phe Asn Lys Gln
```

-continued

```
            50                  55                  60
Ala Ile Arg Arg Leu Lys Thr Glu Ala Gln Met Ser Ile Gln Leu Ile
 65                  70                  75                  80

Asn Lys Ala Val Asn Ala Leu Ile Asn Asp Gln Leu Ile Met Lys Asn
                 85                  90                  95

His Leu Arg Asp Ile Met Gly Ile Pro Tyr Cys Asn Tyr Ser Arg Tyr
            100                 105                 110

Trp Tyr Leu Asn His Thr Ser Thr Gly Lys Thr Ser Leu Pro Arg Cys
            115                 120                 125

Trp Leu Ile Ser Asn Gly Ser Tyr Leu Asn Glu Thr Lys Phe Ser Asp
            130                 135                 140

Asp Ile Glu Gln Gln Ala Asp Asn Met Ile Thr Glu Met Leu Gln Lys
145                 150                 155                 160

Glu Tyr Ile Asp Arg Gln Gly Lys Thr Pro Leu Gly Leu Val Asp Leu
            165                 170                 175

Phe Val Phe Ser Thr Ser Phe Tyr Leu Ile Ser Ile Phe Leu His Leu
            180                 185                 190

Val Lys Ile Pro Thr His Arg His Ile Val Gly Lys Pro Cys Pro Lys
            195                 200                 205

Pro His Arg Leu Asn His Met Gly Ile Cys Ser Cys Gly Leu Tyr Lys
            210                 215                 220

Gln Pro Gly Val Pro Val Arg Trp Lys Arg
225                 230
```

<210> SEQ ID NO 17
<211> LENGTH: 388
<212> TYPE: PRT
<213> ORGANISM: SARS VIRUS

<400> SEQUENCE: 17

```
Trp Thr Phe Gly Ala Gly Ala Ala Leu Gln Ile Pro Phe Ala Met Gln
  1               5                  10                  15

Met Ala Tyr Arg Phe Asn Gly Ile Gly Val Thr Gln Asn Val Leu Tyr
                 20                  25                  30

Glu Asn Gln Lys Gln Ile Ala Asn Gln Phe Asn Lys Ala Ile Ser Gln
             35                  40                  45

Ile Gln Glu Ser Leu Thr Thr Thr Ser Thr Ala Leu Gly Lys Leu Gln
 50                  55                  60

Asp Val Val Asn Gln Asn Ala Gln Ala Leu Asn Thr Leu Val Lys Gln
 65                  70                  75                  80

Leu Ser Ser Asn Phe Gly Ala Ile Ser Ser Val Leu Asn Asp Ile Leu
                 85                  90                  95

Ser Arg Leu Asp Lys Val Glu Ala Glu Val Gln Ile Asp Arg Leu Ile
            100                 105                 110

Thr Gly Arg Leu Gln Ser Leu Gln Thr Tyr Val Thr Gln Gln Leu Ile
            115                 120                 125

Arg Ala Ala Glu Ile Arg Ala Ser Ala Asn Leu Ala Ala Thr Lys Met
            130                 135                 140

Ser Glu Cys Val Leu Gly Gln Ser Lys Arg Val Asp Phe Cys Gly Lys
145                 150                 155                 160

Gly Tyr His Leu Met Ser Phe Pro Gln Ala Ala Pro His Gly Val Val
            165                 170                 175

Phe Leu His Val Thr Tyr Val Pro Ser Gln Glu Arg Asn Phe Thr Thr
            180                 185                 190
```

-continued

```
Ala Pro Ala Ile Cys His Glu Gly Lys Ala Tyr Phe Pro Arg Glu Gly
            195                 200                 205
Val Phe Val Phe Asn Gly Thr Ser Trp Phe Ile Thr Gln Arg Asn Phe
210                 215                 220
Phe Ser Pro Gln Ile Ile Thr Thr Asp Asn Thr Phe Val Ser Gly Asn
225                 230                 235                 240
Cys Asp Val Val Ile Gly Ile Asn Asn Thr Val Tyr Asp Pro Leu
                245                 250                 255
Gln Pro Glu Leu Asp Ser Phe Lys Glu Leu Asp Lys Tyr Phe Lys
            260                 265                 270
Asn His Thr Ser Pro Asp Val Asp Leu Gly Asp Ile Ser Gly Ile Asn
            275                 280                 285
Ala Ser Val Val Asn Ile Gln Lys Glu Ile Asp Arg Leu Asn Glu Val
            290                 295                 300
Ala Lys Asn Leu Asn Glu Ser Leu Ile Asp Leu Gln Glu Leu Gly Lys
305                 310                 315                 320
Tyr Glu Gln Tyr Ile Lys Trp Pro Trp Tyr Val Trp Leu Gly Phe Ile
                325                 330                 335
Ala Gly Leu Ile Ala Ile Val Met Val Thr Ile Leu Leu Cys Cys Met
            340                 345                 350
Thr Ser Cys Cys Ser Cys Leu Lys Gly Ala Cys Ser Cys Gly Ser Cys
            355                 360                 365
Cys Lys Phe Asp Glu Asp Asp Ser Glu Pro Val Leu Lys Gly Val Lys
            370                 375                 380
Leu His Tyr Thr
385

<210> SEQ ID NO 18
<211> LENGTH: 175
<212> TYPE: PRT
<213> ORGANISM: EBOLA VIRUS

<400> SEQUENCE: 18

Glu Ala Ile Val Asn Ala Gln Pro Lys Cys Asn Pro Asn Leu His Tyr
1               5                   10                  15
Trp Thr Thr Gln Asp Glu Gly Ala Ala Ile Gly Leu Ala Trp Ile Pro
                20                  25                  30
Tyr Phe Gly Pro Ala Ala Glu Gly Ile Tyr Thr Glu Gly Leu Met His
            35                  40                  45
Asn Gln Asp Gly Leu Ile Cys Gly Leu Arg Gln Leu Ala Asn Glu Thr
        50                  55                  60
Thr Gln Ala Leu Gln Leu Phe Leu Arg Ala Thr Thr Glu Leu Arg Thr
65                  70                  75                  80
Phe Ser Ile Leu Asn Arg Lys Ala Ile Asp Phe Leu Leu Gln Arg Trp
                85                  90                  95
Gly Gly Thr Cys His Ile Leu Gly Pro Asp Cys Cys Ile Glu Pro His
            100                 105                 110
Asp Trp Thr Lys Asn Ile Thr Asp Lys Ile Asp Gln Ile Ile His Asp
            115                 120                 125
Phe Val Asp Lys Thr Leu Pro Asp Gln Gly Asp Asn Asp Asn Trp Trp
        130                 135                 140
Thr Gly Trp Arg Gln Trp Ile Pro Ala Gly Ile Gly Val Thr Gly Val
145                 150                 155                 160
Ile Ile Ala Val Ile Ala Leu Phe Cys Ile Cys Lys Phe Val Phe
                165                 170                 175
```

```
<210> SEQ ID NO 19
<211> LENGTH: 191
<212> TYPE: PRT
<213> ORGANISM: INFLUENZA VIRUS

<400> SEQUENCE: 19

Gly Leu Phe Gly Ala Ile Ala Gly Phe Ile Glu Asn Gly Trp Glu Gly
1               5                   10                  15

Met Ile Asp Gly Trp Tyr Gly Phe Arg His Gln Asn Ser Glu Gly Thr
            20                  25                  30

Gly Gln Ala Ala Asp Leu Lys Ser Thr Gln Ala Ala Ile Asp Gln Ile
        35                  40                  45

Asn Gly Lys Leu Asn Arg Val Ile Glu Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Lys Thr Arg Arg Gln Leu Arg Glu
        115                 120                 125

Asn Ala Glu Glu Met Gly Asn Gly Cys Phe Lys Ile Tyr His Lys Cys
    130                 135                 140

Asp Asn Ala Cys Ile Glu Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

Glu Leu Lys Ser Gly Tyr Lys Asp Trp Arg Cys Asn Ile Cys Ile
            180                 185                 190

<210> SEQ ID NO 20
<211> LENGTH: 438
<212> TYPE: PRT
<213> ORGANISM: MEASLES VIRUS

<400> SEQUENCE: 20

Phe Ala Gly Val Val Leu Ala Gly Ala Ala Leu Gly Val Ala Thr Ala
1               5                   10                  15

Ala Gln Ile Thr Ala Gly Ile Ala Leu His Gln Ser Met Leu Asn Ser
            20                  25                  30

Gln Ala Ile Asp Asn Leu Arg Ala Ser Leu Glu Thr Thr Asn Gln Ala
        35                  40                  45

Ile Glu Ala Ile Arg Gln Ala Gly Gln Glu Met Ile Leu Ala Val Gln
    50                  55                  60

Gly Val Gln Asp Tyr Ile Asn Asn Glu Leu Ile Pro Ser Met Asn Gln
65                  70                  75                  80

Leu Ser Cys Asp Leu Ile Gly Gln Lys Leu Gly Leu Lys Leu Leu Arg
                85                  90                  95

Tyr Tyr Thr Glu Ile Leu Ser Leu Phe Gly Pro Ser Leu Arg Asp Pro
            100                 105                 110

Ile Ser Ala Glu Ile Ser Ile Gln Ala Leu Ser Tyr Ala Leu Gly Gly
        115                 120                 125

Asp Ile Asn Lys Val Leu Glu Lys Leu Gly Tyr Ser Gly Gly Asp Leu
    130                 135                 140
```

```
Leu Gly Ile Leu Glu Ser Arg Gly Ile Lys Ala Arg Ile Thr His Val
145                 150                 155                 160

Asp Thr Glu Ser Tyr Phe Ile Val Leu Ser Ile Ala Tyr Pro Thr Leu
            165                 170                 175

Ser Glu Ile Lys Gly Val Ile Val His Arg Leu Glu Gly Val Ser Tyr
        180                 185                 190

Asn Ile Gly Ser Gln Glu Trp Tyr Thr Thr Val Pro Lys Tyr Val Ala
    195                 200                 205

Thr Gln Gly Tyr Leu Ile Ser Asn Phe Asp Glu Ser Ser Cys Thr Phe
210                 215                 220

Met Pro Glu Gly Thr Val Cys Ser Gln Asn Ala Leu Tyr Pro Met Ser
225                 230                 235                 240

Pro Leu Leu Gln Glu Cys Leu Arg Gly Ser Thr Lys Ser Cys Ala Arg
            245                 250                 255

Thr Leu Val Ser Gly Ser Phe Gly Asn Arg Phe Ile Leu Ser Gln Gly
        260                 265                 270

Asn Leu Ile Ala Asn Cys Ala Ser Ile Leu Cys Lys Cys Tyr Thr Thr
    275                 280                 285

Gly Thr Ile Ile Asn Gln Asp Pro Asp Lys Ile Leu Thr Tyr Ile Ala
290                 295                 300

Ala Asp His Cys Pro Val Val Glu Val Asn Gly Val Thr Ile Gln Val
305                 310                 315                 320

Gly Ser Arg Arg Tyr Pro Asp Ala Val Tyr Leu His Arg Ile Asp Leu
            325                 330                 335

Gly Pro Pro Ile Ser Leu Glu Arg Leu Asp Val Gly Thr Asn Leu Gly
        340                 345                 350

Asn Ala Ile Ala Lys Leu Glu Asp Ala Lys Glu Leu Leu Glu Ser Ser
    355                 360                 365

Asp Gln Ile Leu Arg Ser Met Lys Gly Leu Ser Ser Thr Ser Ile Val
370                 375                 380

Tyr Ile Leu Ile Ala Val Cys Leu Gly Gly Leu Ile Gly Ile Pro Ala
385                 390                 395                 400

Leu Ile Cys Cys Cys Arg Gly Arg Cys Asn Lys Lys Gly Glu Gln Val
            405                 410                 415

Gly Met Ser Arg Pro Gly Leu Lys Pro Asp Leu Thr Gly Thr Ser Lys
        420                 425                 430

Ser Tyr Val Arg Ser Leu
        435

<210> SEQ ID NO 21
<211> LENGTH: 199
<212> TYPE: PRT
<213> ORGANISM: HIV

<400> SEQUENCE: 21

Ala Val Gly Ile Gly Ala Leu Phe Leu Gly Phe Leu Gly Ala Ala Gly
1               5                   10                  15

Ser Thr Met Gly Ala Ala Ser Met Thr Leu Thr Val Gln Ala Arg Gln
            20                  25                  30

Leu Leu Ser Gly Ile Val Gln Gln Asn Asn Leu Leu Arg Ala Ile
        35                  40                  45

Glu Ala Gln Gln His Leu Leu Gln Leu Thr Val Trp Gly Ile Lys Gln
    50                  55                  60

Leu Gln Ala Arg Ile Leu Ala Val Glu Arg Tyr Leu Lys Asp Gln Gln
```

```
            65                  70                  75                  80
Leu Leu Gly Ile Trp Gly Cys Ser Gly Lys Leu Ile Cys Thr Thr Ala
                    85                  90                  95

Val Pro Trp Asn Ala Ser Trp Ser Asn Lys Ser Leu Glu Gln Ile Trp
                100                 105                 110

Asn His Thr Thr Trp Met Glu Trp Asp Arg Glu Ile Asn Asn Tyr Thr
                115                 120                 125

Ser Leu Ile His Ser Leu Ile Glu Glu Ser Gln Asn Gln Gln Glu Lys
                130                 135                 140

Asn Glu Gln Glu Leu Leu Glu Leu Asp Lys Trp Ala Ser Leu Trp Asn
145                 150                 155                 160

Trp Phe Asn Ile Thr Asn Trp Leu Trp Tyr Ile Lys Leu Phe Ile Met
                165                 170                 175

Ile Val Gly Gly Leu Val Gly Leu Arg Ile Val Phe Ala Val Leu Ser
                180                 185                 190

Ile Val Asn Arg Val Arg Gln
                195

<210> SEQ ID NO 22
<211> LENGTH: 22
<212> TYPE: PRT
<213> ORGANISM: Artificial sequence
<220> FEATURE:
<223> OTHER INFORMATION: Synthetic peptide

<400> SEQUENCE: 22

Gly Asn His Ile Leu Ser Leu Val Gln Asn Ala Pro Tyr Gly Leu Tyr
1               5                   10                  15

Phe Ile His Phe Ser Trp
                20

<210> SEQ ID NO 23
<211> LENGTH: 19
<212> TYPE: PRT
<213> ORGANISM: Artificial sequence
<220> FEATURE:
<223> OTHER INFORMATION: Synthetic peptide

<400> SEQUENCE: 23

Gly Tyr Phe Val Gln Asp Asp Gly Glu Trp Lys Phe Thr Gly Ser Ser
1               5                   10                  15

Tyr Tyr Tyr

<210> SEQ ID NO 24
<211> LENGTH: 22
<212> TYPE: PRT
<213> ORGANISM: Artificial sequence
<220> FEATURE:
<223> OTHER INFORMATION: Synthetic peptide

<400> SEQUENCE: 24

Gly Tyr His Leu Met Ser Phe Pro Gln Ala Ala Pro His Gly Val Val
1               5                   10                  15

Phe Leu His Val Thr Tyr
                20

<210> SEQ ID NO 25
<211> LENGTH: 19
<212> TYPE: PRT
<213> ORGANISM: Artificial sequence
<220> FEATURE:
```

<223> OTHER INFORMATION: Synthetic peptide

<400> SEQUENCE: 25

Gly Val Phe Val Phe Asn Gly Thr Ser Trp Phe Ile Thr Gln Arg Asn
1               5                   10                  15

Phe Phe Ser

<210> SEQ ID NO 26
<211> LENGTH: 19
<212> TYPE: PRT
<213> ORGANISM: Artificial sequence
<220> FEATURE:
<223> OTHER INFORMATION: Synthetic peptide

<400> SEQUENCE: 26

Met Phe Pro Pro Trp Ser Ala Ala Ala Gly Val Pro Phe Ser Leu Ser
1               5                   10                  15

Val Gln Tyr

<210> SEQ ID NO 27
<211> LENGTH: 26
<212> TYPE: PRT
<213> ORGANISM: Artificial sequence
<220> FEATURE:
<223> OTHER INFORMATION: Synthetic peptide

<400> SEQUENCE: 27

Gln Asp Ala Ile Lys Lys Leu Asn Glu Ser Tyr Ile Asn Leu Lys Glu
1               5                   10                  15

Val Gly Thr Tyr Glu Met Tyr Val Lys Trp
            20                  25

<210> SEQ ID NO 28
<211> LENGTH: 19
<212> TYPE: PRT
<213> ORGANISM: Artificial sequence
<220> FEATURE:
<223> OTHER INFORMATION: Synthetic peptide

<400> SEQUENCE: 28

Met Tyr Lys Thr Pro Thr Leu Lys Tyr Phe Gly Phe Asn Phe Ser
1               5                   10                  15

Gln Ile Leu

<210> SEQ ID NO 29
<211> LENGTH: 28
<212> TYPE: PRT
<213> ORGANISM: Artificial sequence
<220> FEATURE:
<223> OTHER INFORMATION: Synthetic peptide

<400> SEQUENCE: 29

Ala Ala Cys Glu Val Ala Lys Asn Leu Asn Glu Ser Leu Ile Asp Leu
1               5                   10                  15

Gln Glu Leu Gly Lys Tyr Glu Gln Tyr Ile Lys Trp
            20                  25

<210> SEQ ID NO 30
<211> LENGTH: 15
<212> TYPE: PRT
<213> ORGANISM: Artificial sequence
<220> FEATURE:
<223> OTHER INFORMATION: Synthetic peptide -continued

```
<400> SEQUENCE: 30

Asn Tyr Ser Lys Tyr Trp Tyr Leu Asn His Thr Thr Thr Gly Arg
1               5                   10                  15

<210> SEQ ID NO 31
<211> LENGTH: 19
<212> TYPE: PRT
<213> ORGANISM: Artificial sequence
<220> FEATURE:
<223> OTHER INFORMATION: Synthetic peptide

<400> SEQUENCE: 31

Gly Thr Phe Thr Trp Thr Leu Ser Asp Ser Glu Gly Lys Asp Thr Pro
1               5                   10                  15

Gly Gly Tyr
```

COMPOSITIONS AND METHODS FOR MEASLES VIRUS INHIBITION

CROSS-REFERENCE TO RELATED APPLICATIONS

This application is a division of U.S. application Ser. No. 13/962,524, filed on Aug. 8, 2013, which is a division of U.S. application Ser. No. 13/482,388, filed on May 29, 2012, now U.S. Pat. No. 8,598,116, which is a division of U.S. application Ser. No. 12/378,558, filed on Feb. 17, 2009, now abandoned, which is a continuation of U.S. Ser. No. 10/578,013, filed on May 3, 2006, now U.S. Pat. No. 7,491,793, which is the National Stage of PCT/US2004/36578, filed on Nov. 3, 2004, which claims the benefit of U.S. Provisional Application Ser. No. 60/517,181, filed Nov. 4, 2003, each of which is incorporated herein by reference in its entirety.

FIELD OF THE INVENTION

The present invention relates to a method of preventing or inhibiting viral infection of a cell and/or fusion between the envelope of a virus and the membranes of a cell targeted by the virus (thereby preventing delivery of the viral genome into the cell cytoplasm, a step required for viral infection). The present invention provides methods for identifying a fusion initiation region, or FIR, of the viruses. The present invention provides for a method of identifying the FIR in these viruses. The present invention further provides for methods of preventing infection by a Type I virus by interfering with its FIR.

INCORPORATION OF SEQUENCE LISTING TEXT FILE

This application includes biological sequence information in a Sequence Listing presented in an ASCII text file named "TU-271-DIV-1-SEQ.txt", created on Apr. 12, 2012, and having a file size of 23,569 bytes, which is incorporated herein by reference.

INTRODUCTION

All viruses must bind to and invade their target cells to replicate. For enveloped animal viruses, including RNA viruses having Class I membrane fusion proteins (Type I viruses), the process involves (a) binding of the virion to the target cell, (b) fusion of the envelope of the virus with the plasma membrane or an internal cellular membrane, (c) destabilisation of the viral envelope and cellular membrane at the fused area to create a fusion pore, (d) transfer of the viral RNA through the pore, and (e) modification of cellular function by the viral RNA.

Fusion of the viral membrane and the cell envelope, steps (b) and (c) above, is mediated by the interaction of a viral transmembrane glycoprotein (fusion protein) with surface proteins and membranes of the target cell. These interactions cause conformational changes in the fusion protein that result in the insertion of a viral fusion peptide into the target cell membrane. This insertion is followed by further conformational changes within the fusion protein that bring the viral envelope and cell membranes into close proximity and results in the fusion of the two membrane bilayers.

A virus is unable to spread and propagate within its host if this fusion process is disrupted. Intentional disruption of this fusion process can be achieved by directing peptides and peptide mimics homologous to fusion protein sequences, antibodies that recognize the fusion protein, and other factors that act against the fusion protein.

BACKGROUND OF THE INVENTION

Structural Similarities Among RNA Virus Class I Fusion Proteins.

Hemagglutinin 2 (HA2) of influenza virus, an orthomyxovirus, is the prototypic RNA virus Class I fusion protein and contains an amino terminal hydrophobic domain, referred to as the fusion peptide, that is exposed during cleavage of the hemagglutinin precursor protein. The membrane fusion proteins of RNA viruses from several diverse families, including arenaviruses, coronaviruses, filoviruses, orthomyxoviruses, paramyxoviruses, and retroviruses, share several common structural features with HA2 and have been referred to as Class I viral fusion proteins.

It has been observed that the fusion protein of HIV-1, the transmembrane glycoprotein and other retroviral transmembrane proteins, like those of orthomyxoviruses and paramyxoviruses, possess a hydrophobic fusion peptide domain exposed during cleavage of a precursor (gp160) (Gallaher, 1987; Gonzalez-Scarano et al., 1987). Based on these similarities and computer algorithms that predict protein configurations, it has been suggested (Gallaher et al., 1989) that the external portion (ectodomain, amino terminus) of HIV-1 transmembrane protein and the transmembrane proteins of other retroviruses, all could fit the scaffold of HA2 structure as determined by x-ray crystallography (Wilson, Skehel, and Wiley, 1981).

Based on these observations, it was predicted that retroviral transmembrane proteins contain several structural features in addition to the fusion peptide in common with the known structure of HA2, including an extended amino terminal helix (N-helix, usually a "heptad repeat" or "leucine zipper"), a carboxyl terminal helix (C-helix), and an aromatic motif proximal to the transmembrane domain. The presence of at least four out of these five domains defines a viral envelope protein as a Class I fusion protein. This retroviral transmembrane protein model was subsequently confirmed by structural determinations and mutational analyses (Chan et al., 1997; Kowalski et al., 1991; Weissenhorn et al., 1997). Common structural motifs are present not only in orthomyxovirus and retrovirus fusion proteins, but also in those of paramyxoviruses, filoviruses (such as Ebola virus, EboV) (Gallaher, 1996) and arenaviruses (Gallaher, DiSimone, and Buchmeier, 2001). The Gallaher structural model of the EboV fusion protein (GP2) has also been confirmed by x-ray crystallographic methods (Malashkevich et al., 1999; Weissenhorn et al., 1998).

FIG. 1 shows the five, previously-described, domains of the fusion proteins of the six families of Type I viruses. The fusion proteins originate in a hydrophobic fusion peptide, terminate in an anchor peptide, and incorporate an extended amino terminal alpha-helix (N-helix, usually a "heptad repeat" or "leucine zipper"), a carboxyl terminal alpha-helix (C-helix) (Carr and Kim, 1993; Suarez et al., 2000; Wilson, Skehel, and Wiley, 1981), and sometimes an aromatic motif proximal to the virion envelope. Also shown is the sixth domain, the fusion initiation region (FIR), discovered by the present inventors.

Fusion Inhibition in Type I Viruses.

Previous attempts by the present inventors (Garry) and others to design peptides and peptide mimics, antibodies, and other factors that inhibit fusion in Type I viruses have focused on the fusion peptide, the N-helix, and the C-helix of the fusion proteins. In the case of fusion peptides, analogs of the orthomyxoviruses and paramyxoviruses (Richardson, Scheid, and Choppin, 1980) and HIV-1 fusion peptide domains (Gallaher et al., 1992; Owens et al., 1990; Silburn et al., 1998) have been found to block viral infection, presumably by forming inactive heteroaggregates. Peptides corresponding to portions of the N-helix and C-helix have also been found to be effective in inhibiting viral infection both in vitro and in vivo. For example, a 17-amino-acid peptide corresponding to the carboxy-terminal portion of the N-helix of the HIV-1 fusion protein, defined as the CS3 region, blocked HIV infection (Qureshi et al., 1990). In addition, other N-helix and C-helix inhibitory peptides were developed based on the fusion protein structural model (Wild, Greenwell, and Matthews, 1993; Wild et al., 1992), including the C-helix anti-HIV-1 peptidic drug DP178 (T-20 or FUZEON®). DP178 overlaps the C-helix and the aromatic anchor-proximal domain and inhibits HIV-1 virion: cell fusion at very low concentrations (50% inhibition at 1.7 nM) achievable in vivo following injection. In a clinical trial, 100 mg/day of DP178 caused an approximately 100-fold reduction in plasma HIV-1 load of infected individuals (Kilby et al., 1998). This result has greatly motivated the search for other HIV-1 inhibitory peptides based on transmembrane protein structure (Pozniak, 2001; Sodroski, 1999). Peptidic inhibitors of paramyxoviruses have also been shown to inhibit viral replication (Lambert et al., 1996; Young et al., 1999). Studies by Watanabe and coworkers suggest that a similar approach of targeting the N-helix and the C-helix of EboV GP2 may also lead to useful inhibitors (Watanabe et al., 2000). Neutralizing antibodies directed against portions of the fusion protein domains have also been shown to inhibit virion:cell fusion.

Observations in HIV-1.

A great deal of study has been devoted to fusion inhibition in human immunodeficiency virus HIV-1, one of the Type I RNA viruses. Bolognesi et al. (U.S. Pat. No. 5,464,933) and the present inventors (Garry, U.S. Pat. No. 5,567,805) teach that HIV-mediated cell killing can be inhibited by introducing peptides that bind to portions of the transmembrane fusion protein of the HIV-1 virion. The Bolognesi DP178 binding region, labeled FUZEON® in FIG. 7, lies primarily on the C-helix and is outside what is described in the present application the fusion initiation region (FIR). Bolognesi demonstrates inhibition but teaches no method of inhibition. The present inventors (Garry) previously demonstrated inhibition at the CS3 region of HIV-1™, labeled CS3 in FIG. 7, but identified no method of inhibition, suggesting only that CS3: CS3-receptor interaction is inhibited. The unexpected discovery of the FIR by the present inventors (as currently described herein) and the fact that the CS3 sequences lie within the FIR indicates that the CS3: CS3-receptor binding described in U.S. Pat. No. 5,567,805 is in fact binding that occurs between the CS3 portion of the FIR and portions of the cell membrane for which the CS3 portion of the FIR has an affinity. In addition, although Melikyan, Watanabe, Bewley, and others have described fusion inhibition with introduced peptides, they have not explained the mechanisms through which the inhibition occurs. Correspondingly, the location of the FUZEON® peptide is distant from the FIR, which strongly suggests that other elements of the fusion process operate in the FUZEON® region.

In view of the foregoing, it is clear that there exists a need in the art for a more effective means for identifying those regions of viruses that are involved in the infection process and for compositions effective for preventing or inhibiting viral infection. The invention described and disclosed herein provides an effective solution to these needs.

SUMMARY OF THE INVENTION

Various embodiments of the instant invention provide for methods of identifying "factors" (compounds) capable of inhibiting membrane fusion between viruses and their host cells and, thereby, preventing or inhibiting infection of the host cell by the virus. Aspects of this embodiment of the invention provide for methods of identifying these inhibitory "factors" where the method comprises the steps of (a) identifying a virus having an envelope fusion protein having two, or more, extended alpha helices, a fusion peptide, and a fusion initiation region (FIR); (b) preparing a "target" wherein the target comprises the amino acid sequence of the FIR, (c) exposing the "target" to one or more test compounds, and (d) identifying those test compounds that physically interact with the "target". For example, physical interaction can be detected using a "target" bound to a solid substrate and a fluorescently or radioactively labeled test compound in a standard binding assay. Target and test compounds having dissociation coefficients ($K_d$) in the micromolar range or lower (i.e. ≤about $9 \times 10^{-6}$) are considered to be positively interacting.

Other aspects of the instant invention provide for compositions comprising an isolated peptide having the amino acid sequence of a viral fusion initiation region (FIR) or a functional segment of the FIR or having an amino acid sequence which is analogous to the sequence of a FIR or a functional segment of a FIR. As used herein, an analogous amino acid or peptide sequence is a sequence containing a majority of identical or chemically similar amino acids in the same order as a primary sequence. Such chemical similarities are well known to those skilled in the art.

Other aspects of this embodiment of the invention provide for isolated, typically substantially purified, peptides or peptide analogs that are capable of preventing or inhibiting viral infection of a host cell and/or inhibiting membrane fusion of a virus with a host cell, where the virus comprises a membrane fusion protein having two (extended) alpha helices, a fusion peptide and a FIR.

Additional embodiments of the instant invention provide for methods of treating or preventing viral infection by administering to a patient one or more of the compounds identified by the methods described herein as capable of inhibiting viral infection. In various aspects of this embodiment of the invention the compounds administered are peptides or peptide analogs comprising all or a functional segment of a viral FIR sequence. In any aspect of this embodiment of the invention the administered compound is antigenic and is administered in an amount sufficient to eliciting an immune response.

Other embodiments of the instant invention provide for a "molecular factor", such as a plasmid, recombinant virus, or other substance which enables or stimulates a cell or organism to produce a peptide or peptide analog that is capable of preventing or inhibiting a viral infection of that cell or organism. In any aspect of this embodiment the "molecular factor" is capable of preventing or inhibiting a viral infection when administered to a patient.

Another embodiment of the instant invention provides for antibodies capable of inhibiting the virus:cell membrane fusion of a virus having a fusion protein comprising two, extended alpha-helices, a fusion peptide and a FIR. In any aspect of this embodiment of the invention the antibodies are capable of binding specifically to amino acid sequences comprising the FIR sequence, or fragments thereof of sufficient size to allow antibody recognition. Various aspects of this embodiment of the invention provide for methods of producing the antibodies. In certain aspects of this embodiment, the method for producing antibodies comprises: (a) providing as the antigen a peptide comprising a viral initiation region (FIR) or an antigenic fragment of the FIR; (b) introducing the antigen in to an animal so as to elicit an immune response; (c) collecting antibodies from the animal; and optionally, (d) purifying the collected antibodies to identify that fraction of the collected antibodies having a high specificity for the antigen.

Other embodiments of the current invention provide methods of treating patients, which methods comprise administering to the patient antibodies that specifically recognize and bind to peptides comprising a FIR region from a virus or comprising a functional fragment of such a FIR region where the functional fragment is of sufficient size to allow its specific recognition by an antibody (that is, it is an antigenic fragment).

Other embodiments of the instant invention provide for methods of producing antibodies specific for FIR or functional fragments thereof.

BRIEF DESCRIPTION OF THE FIGURES

FIGS. 2 through 7 show the amino acid sequences of these fusion proteins (corresponding to SEQ ID NOs 16-21, respectively) and a schematic representation of their ectopic structure. Specifically shown are the five previously-described domains are the fusion peptide, i.e., the N-helix, the C-helix, the aromatic motif (if present), and the anchor peptide. The newly-discovered sixth domain, the fusion initiation region, or FIR is also identified. Each FIR is indicated by a polygon in FIGS. 2 through 7. The circled area behind the fusion proteins in each of FIGS. 2-7 represents the primary virus:cell binding protein (VCBP) of the virus. The VCBP usually interacts with the portion of the fusion protein which is most distal from the viral membrane and is thus shown to be so positioned in the Figures. Unlike the highly-conserved fusion protein, the VCBP of each virus family is more divergent. It is usually the VCBP that dictates the host range of the virus and determines which of the host's cell types are targeted for infection. The VCBP acts in this capacity by recognizing and binding with specific cell surface proteins. The binding of the VCBP to the targeted cell proteins occurs prior to and is typically a prerequisite for virus:cell fusion.

FIG. 9: Inhibition of Lassa virus infectivity by fusion initiation region peptides. Between 50 and 100 PFU Lassa virus was pre-incubated with or without the indicated peptides (approximately 100 µM) in serum-free BME for 1 hour. Cells were then exposed to the peptide-treated inoculum or vehicle control (no peptide). After 1 hour adsorption, the inoculum was removed, cells were washed twice with 1× phosphate buffered saline, and the cells were overlaid with BME containing 5% FBS, 10 mM HEPES and 0.5% agarose. Four days after infection a second overlay containing 5% neutral red was applied, and plaques were counted 24 hours later.

ILLUSTRATIVE EMBODIMENTS OF THE INVENTION

Figure 1:
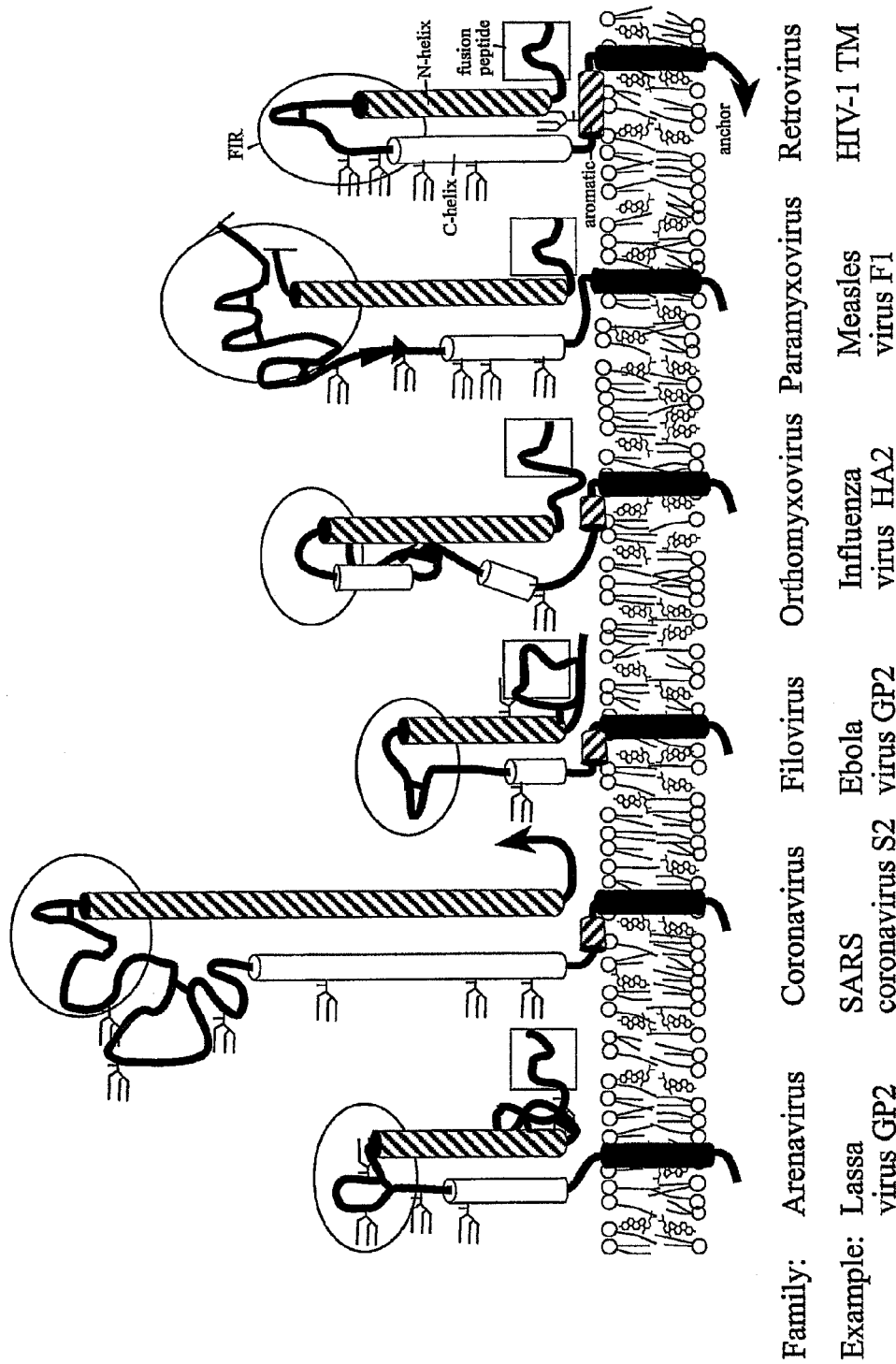
FIG. 1 shows the domains of the fusion proteins of one member of each of these six viral families (namely, arenaviruses, coronaviruses, filoviruses, orthomyxoviruses, paramyxoviruses, and retroviruses). The circles in FIG. 1 show the approximate location of the FIR in each virus illustrated.

The Sixth Domain of RNA Viruses Having Class I Membrane Fusion Proteins.

The arenaviruses, coronaviruses, filoviruses, orthomyxoviruses, paramyxoviruses, and retroviruses are the six families of RNA viruses currently identified that have Class I membrane fusion envelope proteins. The fusion proteins of these Type I viruses have previously been shown by the present inventors (Garry) and others to incorporate five conserved motifs, or domains (Carr and Kim, 1993; Gallaher et al., 1989; Suarez et al., 2000; Wilson, Skehel, and Wiley, 1981). These domains comprise a fusion peptide, an N-helix, a C-helix, and an aromatic motif, all of which are ectodomains, and an anchor peptide, which is an endodomain.

Using computational analyses, secondary structure models, interfacial hydrophobicity calculations and other techniques, the present inventors have made the surprising discovery of a highly conserved sixth domain that is present in the fusion proteins of a wide variety of viruses (this sixth domain is described herein). The viruses possessing this domain include, but are not necessarily limited to the six classes of RNA viruses listed above. To emphasize the critical function of this newly identified domain, which is an ectodomain, the domain is referred to herein as the fusion initiation region (FIR) of the viruses.

Various embodiments of the instant invention provide methods of identifying the FIR in arenavirus, coronavirus, filovirus, orthomyxovirus, paramyxovirus, and retrovirus families of viruses. Also provided are methods of determining whether the FIR is present in other known virus families or in any newly discovered virus families.

As used herein the term "extended" alpha helix refers to an alpha helix having more than four "alpha helix turns" (specifically, more than 14 amino acids).

Other embodiments provide for "factors" that the inventors have unexpectedly found are effective for preventing or inhibiting viral infection and/or virus:cell fusion.

As used herein the term "factors" includes, but is not limited to isolated peptides or functional peptide segments (or peptide analogs thereof) of the newly described fusion initiation region (FIR) domains, peptide mimics ("peptide mimic" refers to any compound or substance that could serve as a substitute for a peptide interacting with the FIR, that is any compound that mimics the properties of a functional segment of the FIR), antibodies specific for functional FIR domains (e.g. idiotypic or anti-idiotypic antibodies) and other molecular compounds that interfere with virus:cell binding and/or fusion.

As used herein the term "functional segment" or "functional fragment" of a fusion initiation region (FIR) refers to a fragment capable of inhibiting virus:cell fusion, inhibiting viral infectivity, capable of eliciting an antibody capable of recognizing and specifically binding to the FIR and/or interfering with FIR-mediated cell infection.

As used herein, a "peptide analog" or "modified peptide" is preferably defined as a FIR peptide modified to contain an amino group, an acetyl group, a hydrophobic group (for example carbobenzoxyl, dansyl, or t-butyloxycarbonyl) or a macromolecular carrier group (for example lipid conjugate, polyethylene glycol, a carbohydrate or a protein) at the amino terminus. An additional class of FIR peptide analogs contains a carboxyl group, an amido group, a hydrophobic group or a macromolecular carrier group at the carboxyl terminus. Other peptide analogs are defined as FIR peptides wherein at least one bond linking adjacent amino acids residues is a non-peptide bond (for example an imido, ester, hydrazine, semicarbazoide or azo bond), a peptide wherein at least one amino acid residue is in a D-isomer configurations or a peptide in which the order of the amino acids is inverted. Additional peptide analogs are FIR peptides compromising at least one amino acid substitution wherein a first amino acid residue is substituted for a second, different amino acid residue (the amino acid substitution can be a conserved substitution or a non-conserved substitution). As used herein, such peptide analogs may comprise analogous amino acid sequences in which the analogous sequences contain a majority of identical or chemically similar amino acids in the same order as the primary sequences.

As used herein, the term "fusion initiation region" (FIR) generally refers to a region of a viral fusion protein involved in the initial step or steps of viral infection and/or fusion with a host cell.

As used herein the term "peptide mimic" includes, but is not limited to organic compounds or other chemicals that mimic the structure or function of the FIR peptide. Examples of peptide mimics include, but are not limited to organic compounds comprising the functional side-groups of an amino acid or peptide, but lacking the carbon/nitrogen backbone or peptide bonds. Peptide mimic also refers to compounds that mimic the action of these functional side-groups with other moieties.

Other molecules, such as idiotype or anti-idiotype antibodies or proteins selected via phage display methods, that bind to the peptides, peptide analogs or peptide mimics described in the present application may also function as inhibitors of viral infection and/or virus:cell fusion. Also contemplated by the instant invention are plasmids, or recombinant viruses, or other molecules or compounds that enable or stimulate the patient to produce an analog of the inhibitory compounds. For example, a recombinant protein, produced in an engineered bacterial, fungal, or mammalian cell, can be used to produce an immunogenic analog of the FIR of a viral fusion protein. Similarly, an anti-idiotypic response could be induced in the individual by using an engineered protein comprising a sequence corresponding to the binding site of a FIR-specific antibody.

As used herein the term "fusion peptide" preferably refers to a hydrophobic sequence at or near the amino terminus of a class I viral fusion protein (see, Gallaher et al., 1987; 1992).

As used herein the term "substantially purified" peptide or peptide analog preferably refers to a peptide or peptide analog that is greater than about 80% pure. More preferably, "substantially purified" refers to a peptide or peptide analog that is greater than about 90% or greater than about 95% pure. Most preferably it refers to a peptide or peptide analog that is greater than 96%, 97%, 98%, or 99% pure. Functionally, "substantially purified" means that it is free from contaminants to a degree that makes it suitable for the purposes provided herein. Methods for assessing purity are well known to those of skill in the art. Suitable methods include, but are not limited to gas chromatography (GC) linked mass spectrophotometry, high performance liquid chromatography (HPLC) analysis, and functional assays in cell culture systems that, inter alia, assess cytotoxicity.

As used herein the term "stable analog" refers to a peptide that has a pharmacologically active half-life in biological systems. Biological half-lives of greater than 60 minutes are contemplated.

As used herein the term "peptide derivative" refers to a peptide that has substituted amino acids different from those in the FIR sequence of a viral fusion protein. Wherein the substitutions do not render the peptide useless for the instant invention.

According to various aspects of the present embodiment of the invention the peptides, peptide analogs, peptide mimics, and other factors may be produced by any means known in the art, including, but not limited to, chemical synthesis, recombinant DNA methods and combinations thereof.

The present invention provides methods for identifying the FIR of Type I, and other, viruses and for treating or preventing infection by these viruses. One possible mechanism by which the current invention may to prevent and/or inhibit infection is by interfering with the FIR mediated virus:cell fusion. The six families of RNA viruses now known to have Class I membrane fusion proteins (Type I viruses) and representative members of each family are listed in Table 1 and Table 2.

TABLE 1

Representative RNA Viruses Having Class I Membrane Fusion Proteins
(Type I Viruses)

| Family | Representative Virus | Shown in FIGURES |
|---|---|---|
| Arenaviruses | Lassa Virus | Yes |
| | Lymphocytic Choriomeningitis Virus (LCMV) | No |
| | Junin Virus | No |
| | Machupo Virus | No |
| | Guanarito Virus | No |
| | Sabia Virus | No |
| Coronaviruses | Severe Acute Respiratory Syndrome (SARS) Virus | Yes |
| | Murine Hepatitis Virus (MHV) | No |
| | Bovine Coronavirus | No |
| | Canine Coronavirus | No |
| | Feline Infectious Peritonitis Virus | No |
| Filoviruses | Ebola Virus | Yes |
| | Marburg Virus | No |

TABLE 1-continued

Representative RNA Viruses Having Class I Membrane Fusion Proteins (Type I Viruses)

| Family | Representative Virus | Shown in FIGURES |
|---|---|---|
| Orthomyxoviruses | Influenza A Virus | Yes |
|  | Influenza B Virus | No |
|  | Influenza C Virus | No |
| Paramyxoviruses | Measles Virus | Yes |
|  | Mumps Virus | No |
|  | Canine Distemper Virus | No |
|  | Newcastle Disease Virus | No |
| Retroviruses | Human Immunodeficiency Virus 1 (HIV-1) | Yes |
|  | Human Immunodeficiency Virus 2 (HIV-2) | No |
|  | Human T-cell Lymphotrophic Virus 1 (HTLV-1) | No |
|  | Human T-cell Lymphotrophic Virus 2 (HTLV-2) | No |
|  | Human Intracisternal A-type Particle 1 (HIAP-1) | No |
|  | Human Intracisternal A-type Particle 2 (HIAP-2) | No |

TABLE 2

Illustrated RNA Viruses Having Class I Membrane Fusion Proteins (Type I Viruses) shown in the Figures.

Figure 2:
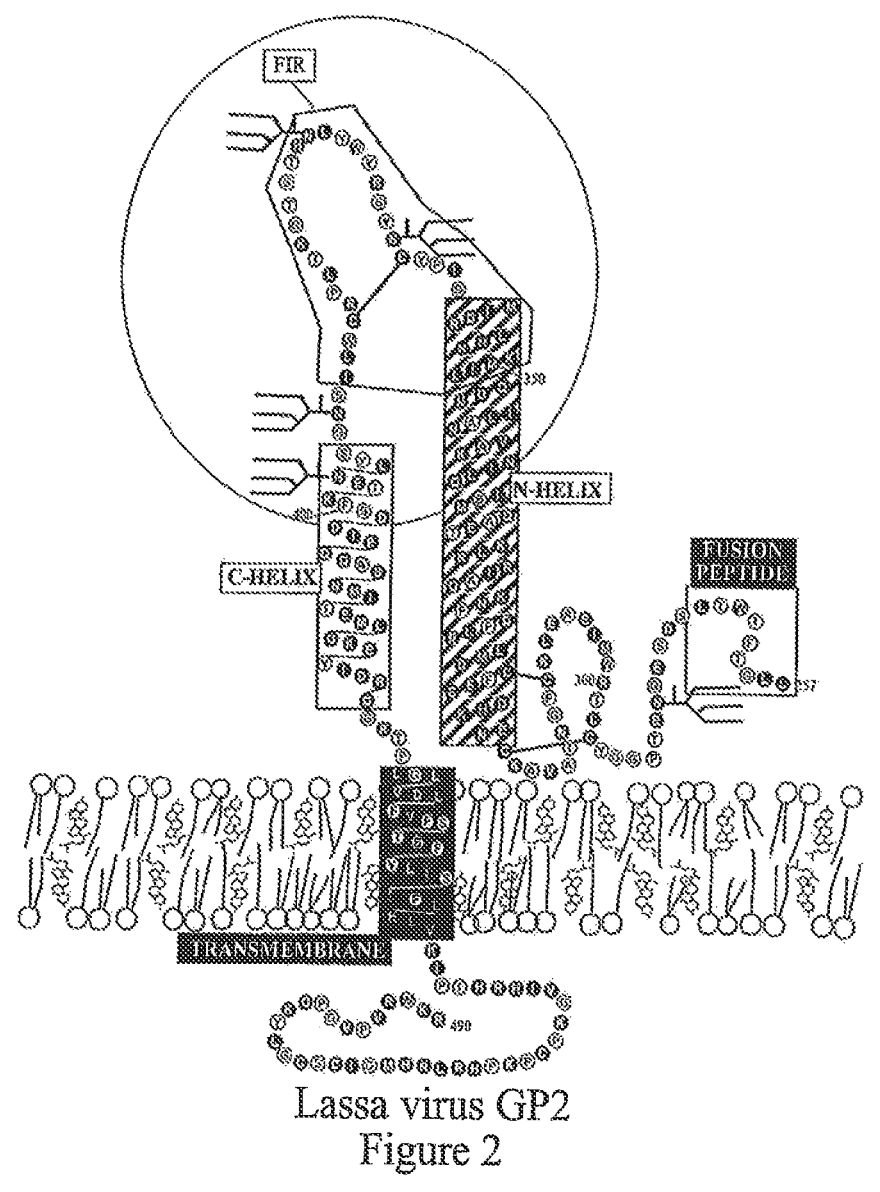
Figure 3:
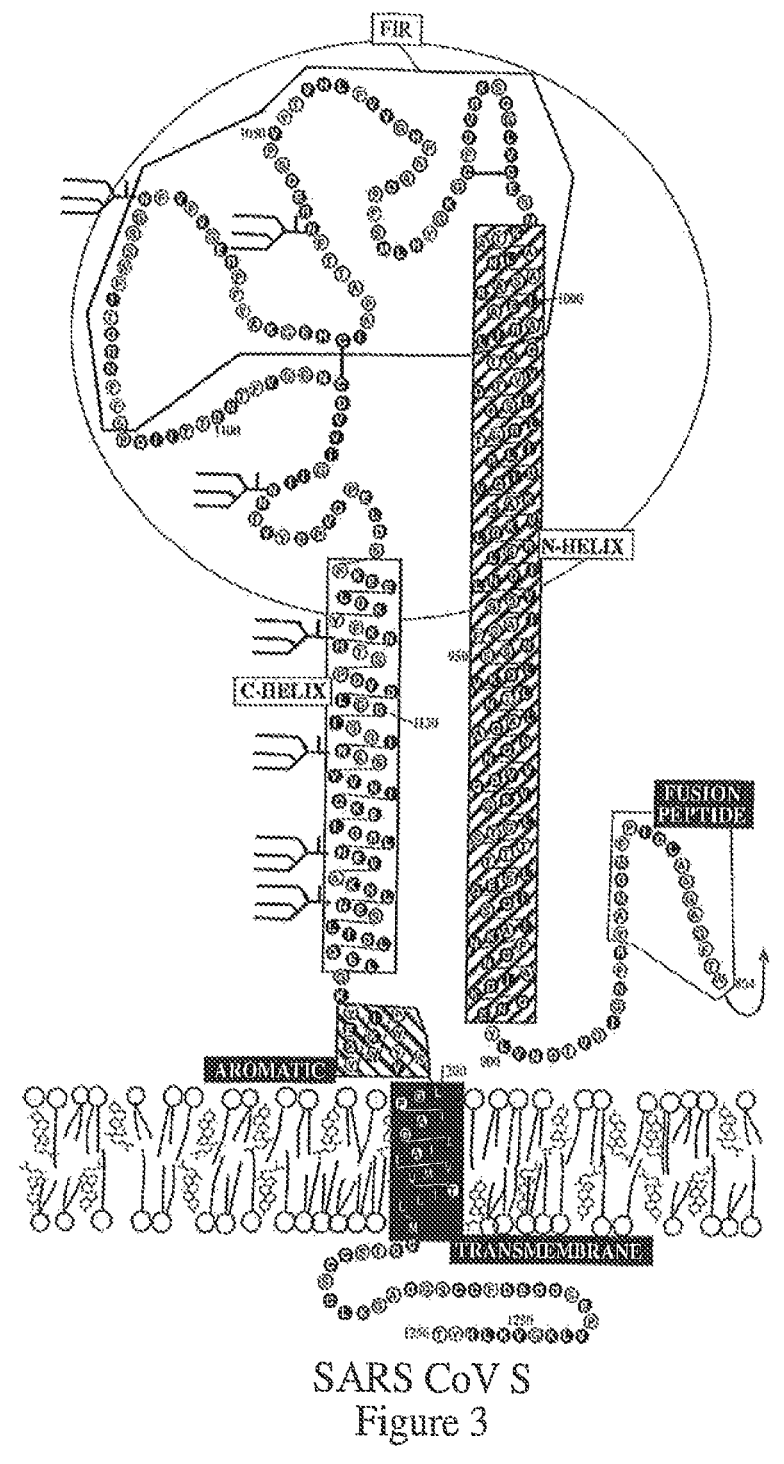
Figure 4:
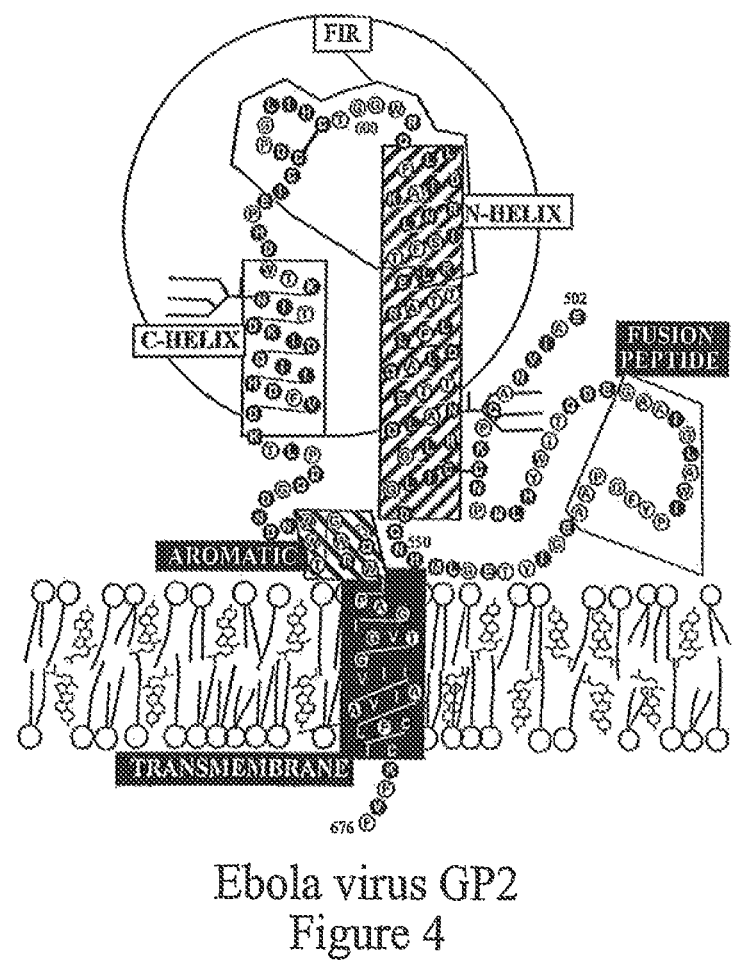
Figure 5:
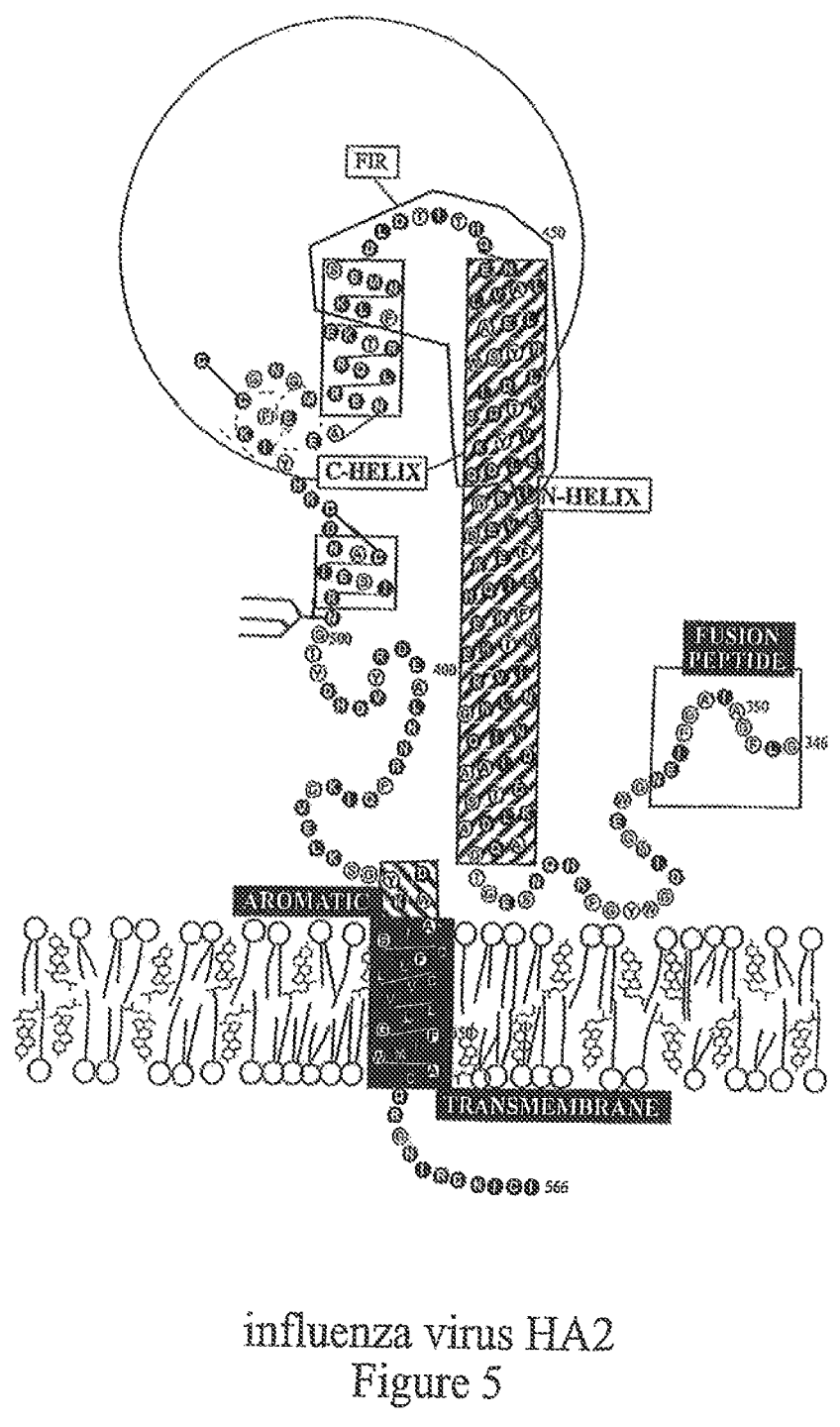
Figure 6:
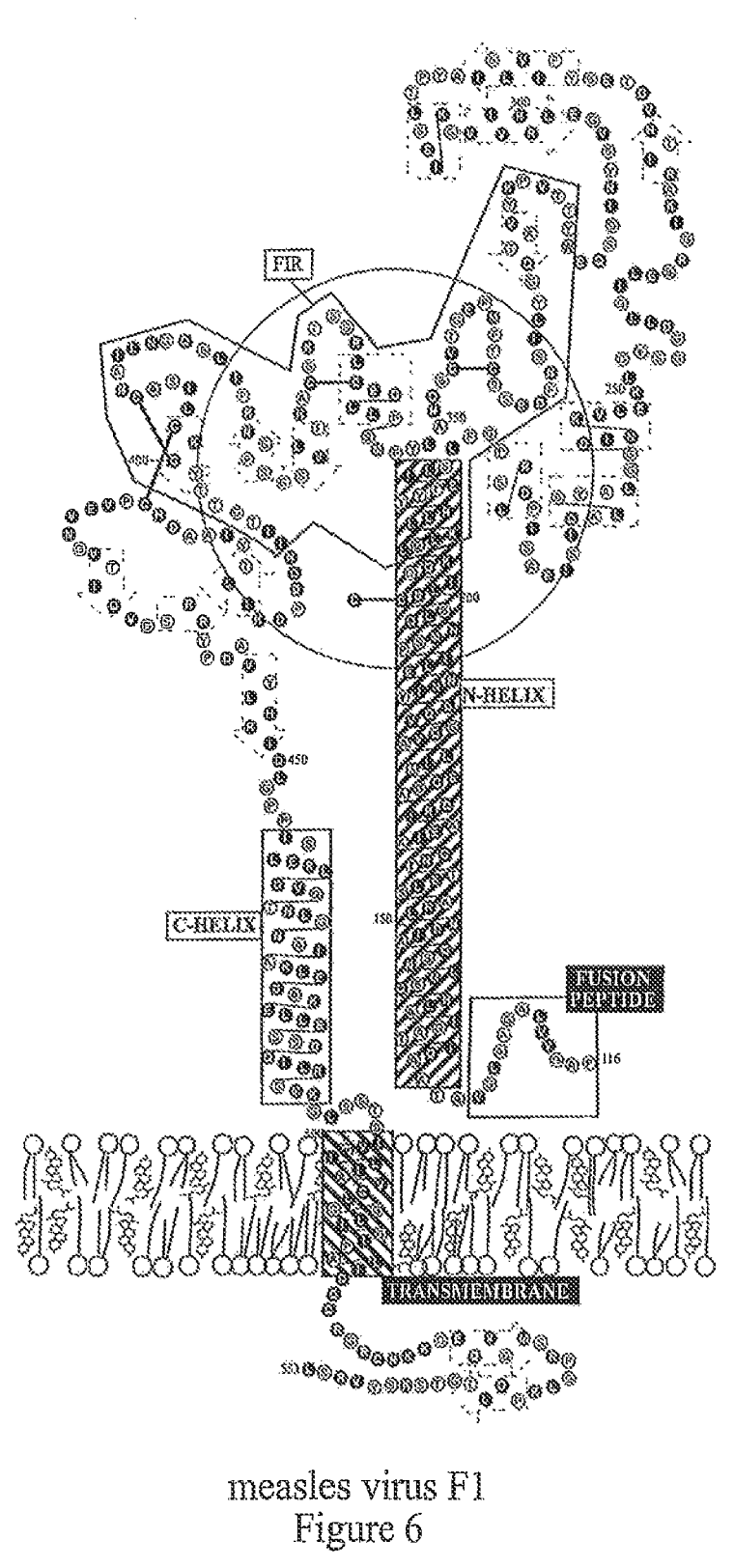
Figure 7:
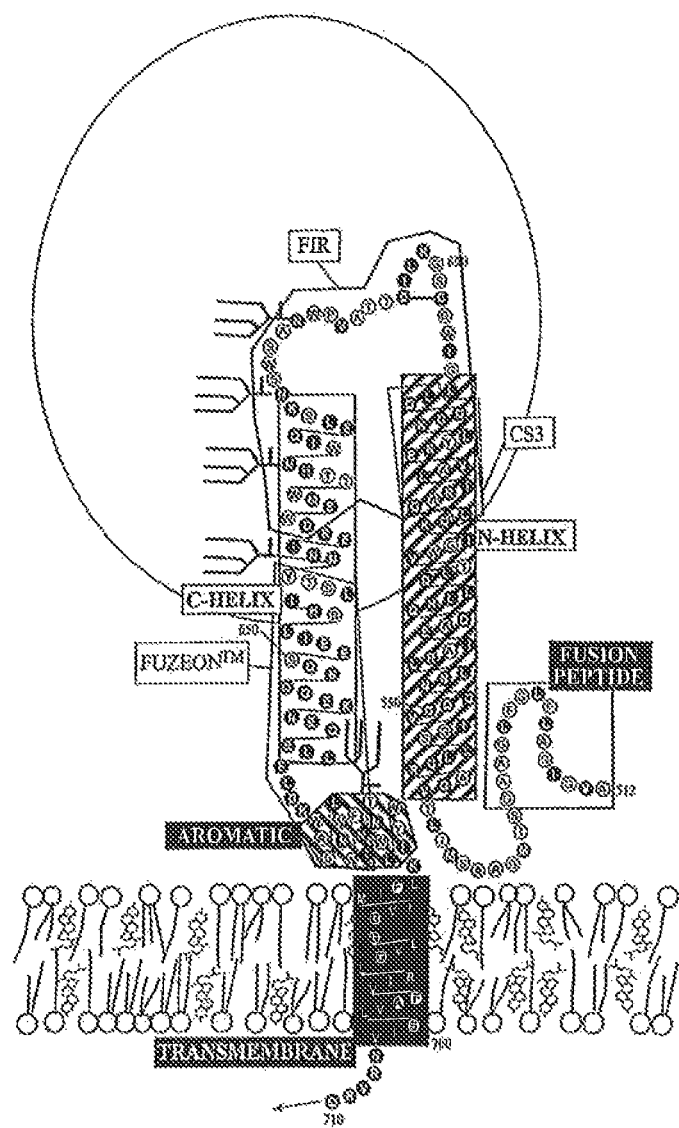

| FIG. | Family | Virus Shown | Protein Shown |
|---|---|---|---|
| FIG. 2 | Arenaviruses | Lassa Virus | GP2 |
| FIG. 3 | Coronaviruses | SARS Virus | S |
| FIG. 4 | Filoviruses | Ebola Virus | GP2 |
| FIG. 5 | Orthomyxoviruses | Influenza A Virus | HA2 |
| FIG. 6 | Paramyxoviruses | Measles Virus | F1 |
| FIG. 7 | Retroviruses | HIV-1 | TM |

The sequences of illustrated Class I membrane fusion proteins (Type I Viruses) shown in the figures are as follows: LASSA GP2 (Genbank Accession Number: A43492, amino acids 257-490), SEQ ID NO: 16; SARS S (Genbank Accession Number: AAQ9406, amino acids 864-1256), SEQ ID NO: 17; EBOLA GP2 (Genbank Accession Number: AAM76034, amino acids 502-676), SEQ ID NO: 18; INFLUENZA HA2 (Genbank Accession Number: P03437, amino acids 346-566), SEQ ID NO: 19; MEASLES F1 (Genbank Accession Number: VGNZMV, amino acids 116-553), SEQ ID NO: 20; HIV™ (Genbank Accession Number: AAB50262, amino acids 512-710), SEQ ID NO: 21.

Method of Identifying the FIR.

Certain embodiments of the invention comprise a method of identifying within the fusion proteins of viruses a conserved motif. The conserved motif of the FIR regions from different viruses will have similar structure and function. Additionally, the FIR regions of related viruses may, but will not necessarily, have highly similar primary amino acid sequences. The current invention provides means for identifying these regions, either with or without relying on their identity/similarity to known sequences.

Other embodiments of the present invention provide for methods useful for preventing or inhibiting viral infection and/or virus:cell fusion using peptides, peptide mimics, antibodies or other factors that are targeted to the specific virus' FIR and interfere with the function of that FIR.

The FIR is typically between 50 and 100 amino acids in length, although it may be longer in some viruses. Various aspects of the current embodiments provide methods for identifying the FIR of a viral fusion protein wherein the methods comprises the following steps: (1) The sequence of the fusion protein is first fitted to the HIV transmembrane fusion protein scaffold, which comprises the N-helix, the C-helix, and other previously-described domains, in order to identify the N-helix and the C-helix in the subject fusion protein. This fitting process is facilitated by searching the primary amino acid sequence of the protein for two or more cysteines that have a propensity to form at least one covalently bonded loop, which will be present in most but not all of these sequences. The N-helix can then be identified in the region preceding this cysteine loop by examining the region for charged amino acids and other amino acids that have the propensity to form an alpha helix (e. g., glutamine (Q), alanine (A), tryptophane (W), lysine (K) and leucine (L)). (2) The amino terminus of the FIR is then identified on the N-helix. This terminus will usually lie within the final 10 to 20 amino acids of the N-helix and will have a core typically comprising three or four hydrophobic amino acids (such as leucine (L) or alanine (A)), a positively-charged amino acid (such as lysine (K) or arginine (R)), a negatively-charged amino acid (such as glutamate (E)), and an aromatic amino acid (such as tyrosine (Y)). (3) The carboxy terminus of the FIR is then identified. In the case of all of the families except the coronaviruses and paramyxoviruses, this terminus is the carboxy-terminus of the first peptide sequence with positive interfacial-hydrophobicity that is found beyond the N-helix. This terminus is usually located beyond the cysteine loop, if the loop is present, and sometimes overlaps the C-helix or is positioned on the C-helix. The positive interfacial-hydrophobicity sequences have a high percentage of aromatic amino acids (such as tryptophane (W), phenylalanine (F), and tyrosine (Y)) and small hydrophobic amino acids (such as glycine (G)). The degree of interfacial hydrophobicity of these sequences can be determined by using the Wimley-White interfacial hydrophobicity scale, preferably with a computer program such as the MPEX program that incorporates this scale. "Interfacial hydrophobicity" is a measure of a peptide's ability to transfer from an aqueous solution to the membrane bilayer interface and is based on the experimentally determined Wimley-White whole-residue hydrophobicity scale (Jaysinghe, Hristova, and White, 2000). Computer programs using this scale can identify a peptide sequence of a peptide chain having positive interfacial hydrophobicity scores and are therefore the most likely to associate with the surface of membranes. See Example 1, as an example of the application of this method to the identification of the FIR in the Ebola virus.

In the case of the coronaviruses, which have longer alpha helices and a generally larger scale, and the paramyxoviruses, in which the FIR is discontinuous because of a non-FIR sequence insert, the carboxy terminus of the FIR is the carboxy-terminus of the second peptide sequence with positive interfacial-hydrophobicity that is found beyond the N-helix. The sequence between the N-helix and C-helix in the F1 protein of paramyxoviruses is longer than the inter-helical sequences of other viruses with Class I viral fusion proteins. The F2 protein of paramyxoviruses, which serves a receptor-binding function, is correspondingly shorter. Upon inspection of computer models, it is obvious to those skilled in the art that the F1 protein contains a sequence insert between the N-helix and C-helix. Consequently, the FIR of paramyxoviruses contains two cysteine loops and two high-interfacial-hydrophobicity sequences and is discontinuous because additional amino acids which are characteristic only of the paramyxoviruses and appear between the N-helix and the first high-interfacial-hydrophobicity sequence are excluded from the FIR.

FIR Sequences.

The sequence of the fusion protein and FIR for each of the six representative viruses shown in FIG. 2 through FIG. 7 is given in the respective Figure and in the Sequence Listing provided below (SEQ ID NO: 16 to SEQ ID NO: 21 provide the respective fusion proteins; and SEQ ID NO: 1 to SEQ NO: 7 provide the respective FIR). Although there is some minor sequence variation among the sister viruses within each of these six families, the FIR in any Type I virus can readily be identified using the representative sequence given in the appropriate figure.

Methods of Inhibiting Fusion in these Viruses.

Other embodiments of the present invention provide methods of inhibiting virus:cell fusion by interfering with the function of the FIR. Various aspects of these embodiments include targeting the FIR with peptides, peptide mimics and other factors which may or may not be analogs of the FIR, in order to interfere with virus:cell fusion. In the various aspects of this embodiment of the present invention the peptides, peptide mimics, and peptide analogs are between about 6 and 150 amino acid residues long. More preferably, they are from about 8 to 50 residues long, even more preferably they are from about 8 to 40 amino acids in length or of such length as is necessary to provide effective inhibition of viral infection. As used herein the term "of such length as necessary to provide effective inhibition of the virus", preferably refers to a length sufficient to provide a 5-fold or greater reduction in viral infectivity, when used according to the instant invention. Methods for quantifying reduction in viral infectivity are well known to those of skill in the art. For example, reductions in viral activity may be determined by plaque reduction, binding inhibition, titer reduction assays, or by animal challenge studies.

FIR peptides, peptides of analogous sequences, or fragments or derivatives thereof, contemplated as being part of the instant invention include, but are not limited to, those comprising, as primary amino acid sequences, all or an efficacious part of one or more of the following: LASSA, X-LIMKNHLRDIMGIPYCNYSRYWYLNHTSTGKTL-PRCWLI-Z (SEQ ID NO: 1); SARS, X-LIRAAEIRASAN-LAATKMSECVLGQSKRVDFCGKGYHLMSFPQAAPH GVVFLHVTYVPSQERNFTTAPAICHEGKAYF-PREGVFVFNGTSWFITQRNFFS-Z (SEQ ID NO: 2); EBOLA, X-LRTFSILNRKAIDFLLQRWGGTCHILGPD-CCI-Z (SEQ ID NO: 3); INFLUENZA, X-IQDLE-KYVEDTKIDLWSYNAELLVALENQHTIDLTD-SEMNKLF-Z (SEQ ID NO: 4), MEASLES, X-LGLKLLRYYTEILSLFG-Z (SEQ ID NO: 5) - - - X-WYTTVPKYV ATQGYLISNFDESSCTFMPEGTVC-SQNALYPMSPLLQECLRGSTKSCARTLVSGSFGN-RFILS QGNLIANCASILCKCYTTGTII-Z (SEQ ID NO: 6), wherein the "- - -" indicates that the Measles FIR is discontinuous; and HIV, X-LQARILAVERYLKDQQLLGI-WGCSGKLICTTAVP WNASWSNKSLE QIWNHT-TWMEWD-Z (SEQ ID NO: 7). In each of the foregoing sequences the "X" and the "Z" respectively designate either the amino- or carboxy-terminus, respectively, of the peptide or an additional moiety, as described below.

Other peptides provided by the instant invention include those having the sequence of a FIR region. In a preferred aspect of this embodiment the FIR region is from a virus belonging to one of the viral families selected from the group consisting of arenaviruses, coronaviruses, filoviruses, orthomyxoviruses, paramyxoviruses, and retroviruses. In a more preferred aspect of this embodiment, the FIR is from a virus selected from the group consisting of Lassa Virus, Lymphocytic Choriomeningitis Virus (LCMV), Junin Virus, Machupo Virus, Guanarito Virus, Sabia Virus, Severe Acute Respiratory Syndrome (SARS) Virus, Murine Hepatitis Virus (MHV), Bovine Coronavirus, Canine Coronavirus, Feline Infectious Peritonitis Virus, Ebola Virus, Marburg Virus, Influenza A Virus, Influenza B Virus, Influenza C Virus, Measles Virus, Mumps Virus, Canine Distemper Virus, Newcastle Disease Virus, Human Immunodeficiency Virus 1 (HIV-1), Human Immunodeficiency Virus 2 (HIV-2), Human T-cell Lymphotrophic Virus 1 (HTLV-1), Human T-cell Lymphotrophic Virus 2 (HTLV-2), Human Intracisternal A-type Particle 1 (HIAP-1), and Human Intracisternal A-type Particle 2 (HIAP-2).

Other aspects of this embodiment of the invention provide for sequences comprising a functional fragment of a FIR sequence or sequences analogous thereto, particularly from a virus belonging to one of the viral families selected from the group consisting of arenaviruses, coronaviruses, filoviruses, orthomyxoviruses, paramyxoviruses, and retroviruses (with the exception of the HIV-1™ CS3 peptide previously described by the present inventors (Garry) and depicted in FIG. 7). In another preferred aspect of this embodiment, the peptide comprises a functional fragment (except the HIV-1™ CS3 fragment) or a sequence analogous to a functional fragment from a virus selected from the group consisting of Lassa Virus, Lymphocytic Choriomeningitis Virus (LCMV), Junin Virus, Machupo Virus, Guanarito Virus, Sabia Virus, Severe Acute Respiratory Syndrome (SARS) Virus, Murine Hepatitis Virus (MHV), Bovine Coronavirus, Canine Coronavirus, Feline Infectious Peritonitis Virus, Ebola Virus, Marburg Virus, Influenza A Virus, Influenza B Virus, Influenza C Virus, Measles Virus, Mumps Virus, Canine Distemper Virus, Newcastle Disease Virus, Human Immunodeficiency Virus 1 (HIV-1), Human Immunodeficiency Virus 2 (HIV-2), Human T-cell Lymphotrophic Virus 1 (HTLV-1), Human T-cell Lymphotrophic Virus 2 (HTLV-2), Human Intracisternal A-type Particle 1 (HIAP-1), and Human Intracisternal A-type Particle 2 (HIAP-2).

As noted above the instant invention also contemplates derivatives of the FIR peptides described above and analogous sequences thereto. These derivative peptides may comprise altered sequences in which functionally equivalent amino acid residues are substituted for residues within the sequence resulting in a silent change. For example, one or more amino acid residues within the sequence can be substituted for by another amino acid of a similar polarity that acts as a functional equivalent, resulting in a silent alteration (e. g. substitution of leucine for isoleucine). Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. By way of further example, and not by way of limitation, such peptides may also comprise D-amino acids, and/or the may comprise an inefficient carrier protein, or no carrier protein at all.

FIR peptides may comprise peptides in which "X" comprises an amino group, an acetyl group, a hydrophobic group or a macromolecular carrier group; and/or "Z" comprises a carboxyl group, an amido group a hydrophobic group or a macromolecular carrier group. Various aspects of the instant invention are drawn to peptides wherein the "X" moiety may also be selected from the group comprising: a hydrophobic moiety, a carbobenzoxyl moiety, dansyl moiety, or a t-butyloxycarbonyl moiety. In any of the peptides of the instant invention the "Z" moiety may be selected from the group comprising: a hydrophobic moiety, a t-butyloxycarbonyl moiety.

In other aspects of this embodiment of the invention the "X" moiety may comprise a macromolecular carrier group. Such macromolecular carrier group may be selected from the group comprising, but not limited to: a lipid conjugate, a polyethylene glycol moiety, or a carbohydrate moiety. Similarly the "Z" may also comprise a macromolecular carrier group; wherein said macromolecular carrier is selected from the group comprising, but not limited to: a lipid conjugate, polyethylene glycol moiety, or a carbohydrate moiety.

Various embodiments of this aspect of the invention also contemplate peptides wherein one or more of the molecular bonds linking adjacent amino acid residues is a non-peptide bond. Such non-peptide bonds include, but are not limited to: imido, ester, hydrazine, semicarbazoide and azo bonds.

Yet other aspects of the instant invention provide for peptides wherein the peptide comprises one or more amino acid residues that is/are in a D-isomer amino acid.

Other aspects of the instant invention provide for peptides comprising one or more amino acid substitution wherein a first amino acid residue is substituted for a second, different amino acid residue, in the sequences provided above (or a functional segment thereof). In various aspects of this embodiment, the amino acid substitution is a conservative substitution. In other aspects of this embodiment the amino acid substitution is a non-conservative substitution. Yet other aspects of this embodiment of the invention provide for peptides as described above except that one or more amino acid residues have been deleted.

In various preferred aspects of the instant embodiments the FIR peptides comprise at least three contiguous residues of a FIR. More preferably the FIR peptide comprises at least 8 contiguous residues of a FIR. As used herein the term "FIR inhibitory peptide(s)" preferably refers to a peptide or peptides having the sequence of a FIR (or functional segment thereof) and to such FIR peptides or functional segments in which one or more amino acids is/are substituted for by functionally equivalent or chemically similar amino acids (see infra). It also refers to derivatives of these peptides, including but not limited to, benzylated derivatives, glycosylated derivatives, and peptides that include enantiomers of naturally occurring amino acids. In a preferred aspect of this embodiment the peptide is selected from those having the sequence of any of SEQ ID NOs 1-7, 8-15, 22-25, and 30. In particularly preferred aspects of this embodiment the peptide has a sequence selected from the group consisting of SEQ ID NOs 22-25 and 30.

In yet other aspects of this embodiment of the invention, the FIR peptides may be linked to a carrier molecule such as a protein, including but not limited to, human serum albumin (HSA).

Furthermore, the instant invention contemplates molecules comprising any combination of the X and Z moieties and/or other peptide modifications described above.

Peptides according to the instant invention may be produced from naturally occurring or recombinant viral proteins. They may also be produced using standard recombinant DNA techniques (e. g. the expression of peptide by a microorganism that contains recombinant nucleic acid molecule encoding the desired peptide, expressed under the control of a suitable transcriptional promoter, and the harvesting of desired peptide from said microorganism). In a preferred aspect of the invention, any of the peptides of the invention may be prepared using any chemical synthesis methodology known in the art including, but not limited to, Merrifield solid phase synthesis (Clark-Lewis et al., 1986, Science 231: 134-139).

Embodiments of the instant invention also provide for other compounds useful for treating or preventing infection of a cell by a virus. These include antibodies (or active segments thereof, meaning portions of antibodies capable of specifically recognizing a FIR region or a functional segment thereof) and other molecules. Certain aspects of this embodiment of the invention provide for antibodies that specifically recognize a FIR, or antigenic fragment thereof and/or are capable of interfering with virus:cell interaction sufficiently to prevent or reduce infection of the cell by the virus. Antibodies according to these embodiments of the invention may be monoclonal or polyclonal.

Various embodiments of the invention provide for methods of producing antibodies capable of specifically recognizing a FIR and/or preventing or reducing infection of the cell by the virus. General methods for producing antibodies are well known to those of skill in the art. Methods for producing antibodies according to the instant invention comprise the steps of (I) providing an antigen comprising a FIR or an antigenic fragment thereof (such antigen may be an unmodified peptide, a peptide mimic, a peptide analog, or a peptide derivative); (ii) exposing the immune system of an animal to the antigen so as to induce an immune response; (iii) collecting antibodies from the animal and identifying those antibodies that either specifically recognize a FIR (or functional segment thereof) and/or are capable of inhibiting or reducing virus:cell infection in a dose responsive manner in assays that measure viral infectivity.

Other embodiment of the instant invention provide for methods of identifying compounds capable of preventing or inhibiting infection by a virus comprising a FIR or that are useful as drug leads for the development of drugs for preventing or inhibiting viral infection. Such methods comprise the steps of: (I) identifying a virus having at least one membrane fusion protein comprising a fusion initiation region that is requisite for virus:cell fusion; (ii) preparing a target, where the target comprises the amino acid sequence of a FIR, or a functional segment of a FIR; (iii) screening a plurality of compounds to identify at least one compound that binds to the target, thereby identifying a target-binding compound; (iv) screening at least one target-binding compound to identify a target-binding compound that is capable of specifically preventing or reducing viral infection by the virus from which the target was obtained or that us useful as a drug lead for the development of a drug for specifically preventing or reducing infection by such a virus. As used herein the phrase "specifically preventing or reducing viral infection" means that the compound specifically prevents infection by the target virus, without any substantial effect on an unrelated virus. For example, if a compound that specifically prevented infection by the SARS virus would not prevent infection by the HIV-1 virus.

As used herein the compounds (e. g. drugs or drug leads) identified by the methods described above may be of any type, by way of non-exclusive list they may be any peptide (or derivative, analog, or mimic thereof) this includes short peptides as are typically employed in phage display libraries, any antibody or active fragment thereof (i.e., any fragment, such as an Fab that is capable of specifically recognizing the target) or any other organic or inorganic molecule.

In any embodiment of the instant invention the FIR may be from any virus having a membrane fusion protein comprising at least extended two alpha-helices, a fusion peptide, and a fusion initiation region. Preferably, the virus is selected from a virus family, wherein the virus family is selected from the group consisting of: arenaviruses, coronaviruses, filoviruses, orthomyxoviruses, paramyxoviruses, and retroviruses. More preferably, the virus is selected from the group consisting of: Lassa virus, SARS (severe acute respiratory syndrome) virus, Ebola virus, influenza virus, measles virus, and HIV-1 (human immunodeficiency virus type 1).

According to various aspects of the instant invention, the peptides and/or factors of the instant invention useful for treating or preventing viral infection of a cell can target the amino acids surrounding and within the FIR cysteine loop, the distal portion of the FIR N-helix, any of the interfacial hydrophobicity regions of the FIR, other areas of the FIR, or any combination of thereof. These factors, antibodies, peptides or peptide analogs (collectively compounds) may be used individually; alternatively they may be used in combinations of two or more to prevent or inhibit infection of the cell by the virus. The methods of preventing or inhibiting viral infection of the cell by interfering with the function of the FIR provided by the instant invention also include the use of neutralizing antibodies, produced exogenously or endogenously, against all or portions of the FIR. The purpose of such use is to interfere with the function of the FIR, thereby inhibiting viral infection of the cell and/or virus:cell membrane fusion.

Other embodiments of the instant invention provide for compositions, including pharmaceutical compositions, comprising any and all of the compounds, peptides (including analogs, derivatives, and mimics thereof), antibodies, or any other molecule of the instant invention or identified by the methods of instant invention. This includes, but is not limited to, compositions containing any molecule that comprises, consists essentially of, or consists of a FIR, or a functional segment of a FIR. It further includes, but is not limited to compositions comprising any compound that specifically recognizes, binds to, or interferes with the function of a viral FIR. As used herein, the phrase "interfering with the function of the FIR" means that a compound interacts with the FIR or with the cellular protein that serves as the receptor that recognizes the FIR so as to prevent or reduce infection of the cell by the virus. Additionally, it is contemplated that the compositions may comprise either one of the molecules described or mixtures of two or more of the molecules.

Further embodiments of the instant invention provide for methods of treating or preventing infection of a cell by a virus (where the virus comprises a FIR) using any of the compounds of the instant invention and/or any compound identified by any of the methods of the instant invention. Various aspects of this embodiment of the invention provide for administering an effective amount of any of the pharmaceutical compositions described herein to a patient suspected of being exposed to a virus (or having potential for being exposed to a virus) wherein the virus comprises a FIR. In various aspects of the invention the pharmaceutical composition comprises an antibody that specifically recognizes and binds to a FIR (or functional segment of a FIR) or a fragment of such antibody that specifically recognizes and binds to a FIR, or functional segment of a FIR.

The peptides of the invention may be administered to patients in any sterile biocompatible pharmaceutical carrier including, but not limited to, saline, buffered saline, dextrose, and water. The peptides of the invention may be administered using techniques well known to those in the art. Preferably the agents are formulated. Techniques for formulation may be found in "Remington's Pharmaceutical Sciences" $18^{th}$ ed., 1990 Mack Publishing Co., Easton, Pa. Methods of introduction include, but are not limited to, transdermal, intramuscular, intraperitoneal, intravenous, subcutaneous, oral and intramucosal administration, including intranasal administration. For transmucosal administration, penetrants appropriate to the barrier to be permeated may be used. Such penetrants are generally known in the art.

Still other aspects of this embodiment of the invention provide for methods that comprise administering to a patient an effective amount of a composition comprising at least one recombinant DNA or RNA molecule; where the RNA or DNA encodes a FIR (or functional segment thereof) or a molecule capable of specifically binding to a FIR or a cellular receptor that recognizes a FIR so as to prevent or reduce infection by the virus. In a preferred aspect of this embodiment the recombinant RNA or DNA molecule and or pharmaceutical composition further comprises the elements necessary to allow the protein encoded by the RNA or DNA molecule to be expressed in a human cell. By way of non-exclusive example, in certain aspects of this embodiment of the invention the recombinant RNA or DNA molecule is part of a recombinant plasmid or a recombinant virus.

Example 1: Identification of the FIR in Ebola Virus

The method to identify the FIR of Class I viral fusion proteins can be illustrated by two examples. The first example is identification of the FIR in the minimal class I fusion protein glycoprotein 2 (GP2) of Ebola virus, a filovirus. The boundaries of the N-helix and the C-helix of Ebola virus GP2 have been determined by x-ray crystallographic methods (Malashkevich et al., 1999). The terminal amino acids of the N-helix contain the sequence ILN-RKAIDF (SEQ ID NO: 8) that fits the consensus of a core comprising three or four hydrophobic amino acids, a positively-charged amino acid, a negatively-charged amino acid, and an aromatic amino acid. Between these two helices are two cysteines in the sequence CHILGPDC (SEQ ID NO: 9). Defining the ends of the Ebola virus GP2 FIR is the sequence FLLQRWGGTCHILGPDCCI (SEQ ID NO: 10), which has a Wimley-White interfacial hydrophobicity score of 2.59 as determined by the MPEX program (Jaysinghe et al, 2002). Thus, the FIR of Ebola virus GP2 extends from amino acids 579 to 610.

Example 2: Identification of the FIR in Measles Virus

The second example is a complex class I fusion protein, the F1 protein of measles virus, a paramyxovirus. The N- and C-helices of measles virus F1 can be identified by examining the primary sequence for amino acids with the propensity to form helices. Alignment of the primary sequence of measles virus F1 with the primary amino acid sequence of the F1 protein of another paramyxovirus, Newcastle disease virus F1, can also aid in the identification of the helix boundaries. The structure of the Newcastle disease virus F1 protein has been determined by x-ray crystallographic methods (Chen et al., 2001). The boundaries of the N- and C-helices can thus be predicted to be amino acids 131-217 and 455-491 respectively. In contrast to Ebola virus GP2 and most other viral class I fusion proteins, the primary sequence between the N- and C-helices in the measles virus is longer than 100 amino acids. The FIR region of measles virus F1 contains an insertion which, upon inspection of computer models, is obvious to those skilled in the art, and thus the FIR structure is formed by a secondary arrangement that brings together two parts of the primary sequence. The inserted sequence forms a loop external to the FIR. The terminal amino acids of the N-helix contain the sequence LKLLRYYTE (SEQ ID NO: 11) which fits the consensus of a core comprising three or four hydrophobic amino acids, a positively-charged amino acid, a negatively-charged amino acid, and an aromatic amino acid. There are eight cysteine residues in measles virus F1 between the N- and C-helices. On the basis of the alignment with Newcastle disease virus F1 it can be determined that the first two cysteines and the second two cysteines form disulfide-linked loops. The first pair of cysteines in the sequence, CTFMPEGTVC (SEQ ID NO: 12), is part of the FIR because it is bounded by a sequence WYTTVPKYVATQGYLISNF (SEQ ID NO: 13) with a Wimley-White interfacial hydrophobicity score of 3.36, as determined by the MPEX program. The second pair of cysteines in the sequence, CLRGSTKSC (SEQ ID NO: 14), is also part of the FIR because it is adjacent to a sequence TLVSGSFGNRFILSQGNLIANCASILCKCYTT-GTII (SEQ ID NO: 15) with a Wimley-White interfacial hydrophobicity score of 2.54, as determined by the MPEX program. Thus, the FIR of measles virus F1 extends from amino acids 205 to 407, with amino acids 221 to 314 representing an insertion that does not participate in FIR function.

Example 3: Identification of Coronavirus Fusion Inhibitory Peptides. Background

Severe acute respiratory syndrome (SARS) is a newly recognized illness that spread from southern China in late 2002/early 2003 to several countries in Asia, Europe and North America (Guan et al., 2004). SARS usually begins with a fever greater than 38° C. Initial symptoms can also include headache, malaise and mild respiratory symptoms. Within two days to a week, SARS patients may develop a dry cough and have trouble breathing. Patients in more advanced stages of SARS develop either pneumonia or respiratory distress syndrome. In the initial outbreak there were 8098 cases worldwide, with an overall mortality of 9.6%. A previously unrecognized coronavirus (CoV) has been demonstrated to be the cause of the new disease (Poutanen et al., 2003; Peiris et al., 2003; Drosten et al., 2003; Rota et al., 2003; Mara et al., 2003). Public health interventions, such as surveillance, travel restrictions and quarantines, contained the original spread of SARS CoV in 2003 and again appear to have stopped the spread of SARS after the appearance of a few new cases in 2004. It is unknown, however, whether these draconian containment measures can be sustained with each appearance of the SARS CoV in humans. Furthermore, the potential of this new and sometimes lethal CoV as a bio-terrorism threat is obvious.

Coronaviruses are large positive-stranded RNA viruses typically with a broad host range. Like other enveloped viruses, CoV enter target cells by fusion between the viral and cellular membranes, a process mediated by the viral spike (S) protein. CoV S proteins, characterized to date, appear to consist of two non-covalently associated subunits, S 1 and S2. Using computational analysis, Garry and Gallaher (2003) first proposed that the portion of the SARS-CoV S protein corresponding to the S2 subunit fit the prototypical model of a class I viral fusion protein based on the presence of two predicted alpha helical regions at the N- and C-terminal regions of S2 (N-helix, C-helix) and an aromatic amino acid-rich region just prior to the transmembrane anchor domain.

Materials And Methods.

L2 cells or Vero E6 cells were maintained as monolayers in complete Dulbecco's modified Eagle's medium (DMEM) containing 0.15% $HCO_3$-supplemented with 10% fetal bovine serum (FBS), penicillin G (100 U/ml), streptomycin (100 mg/ml), and 2 mM of L-glutamine at 37° C. in a 5% $CO_2$ incubator. Mouse hepatitis virus (MHV) strain A59 or SARS CoV strain Urbani or HK was propagated on L2 cells. For plaque assays, L2 cells or Vero E6 cells were seeded at a density of $1\times10^6$ cells in each well of a 6-well plate. Fifty to 100-plaque forming units (PFU) of MHV or SARS CoV were pre-incubated with or without approximately 100, mg/ml of peptide in serum-free DMEM for 1 hour. Cells were then infected with peptide-treated inoculum or vehicle control inoculum. After 1 hour adsorption, the inoculum was removed, cells were washed twice with 1× phosphate buffered saline, and the cells were overlaid with 10% FBS/DMEM containing 0.5% SEAPLAQUE® agarose (Cambrex Bio Science Rockland, Inc., Rockland, Me.). Monolayers were fixed with 3.7% formalin and stained with 1× crystal violet 2 days post-infection, and plaque numbers were determined by light microscopy.

Results And Discussion.

Figure 8:
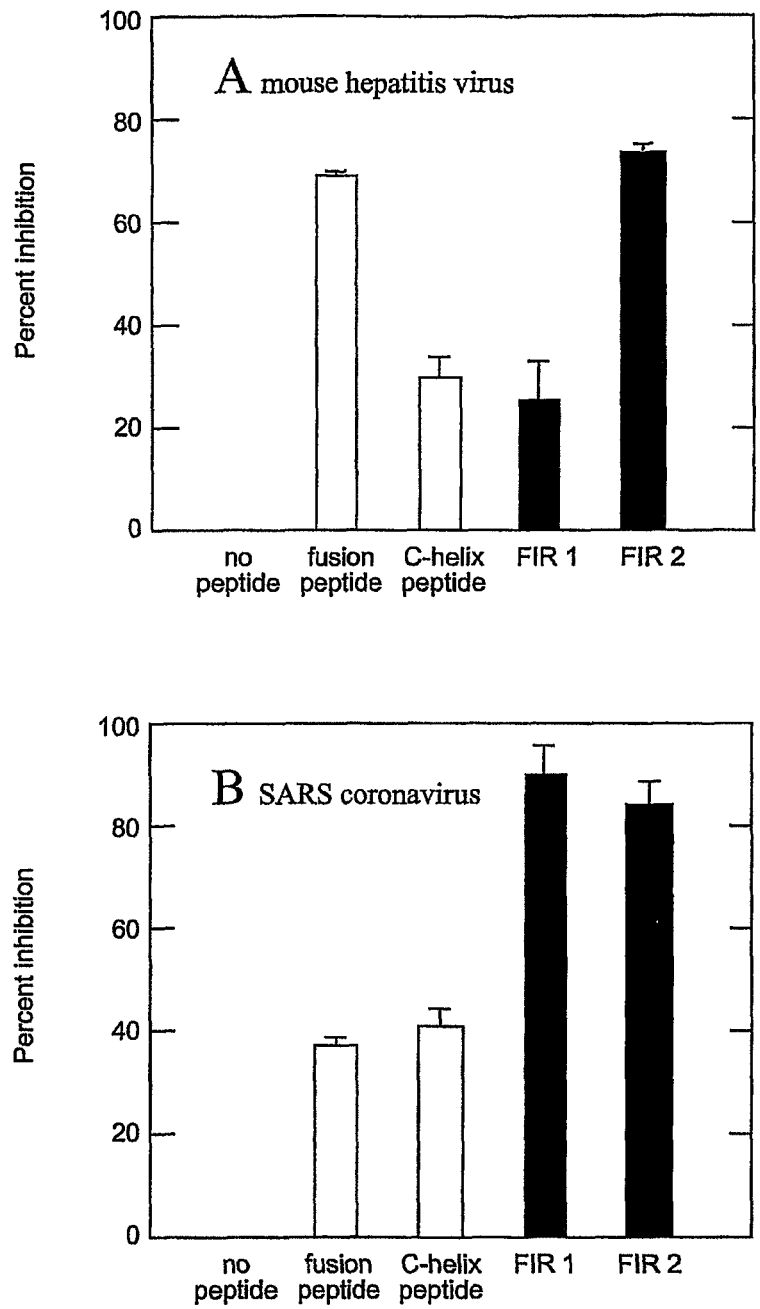
FIG. 8: Inhibition of coronavirus infectivity by fusion initiation region peptides. Between 50 and 100 plaque forming units (PFU) of mouse hepatitis virus strain A59 or SARS coronavirus strain Urbani were pre-incubated with or without the indicated peptides (approximately 100 µM) in serum-free DMEM for 1 hour. Cells were then exposed to peptide-treated inoculum or a vehicle control (no peptide). After 1 hour adsorption, the inoculum was removed, cells were washed twice with 1× phosphate buffered saline, and the cells were overlaid with DMEM containing 10% FBS and 0.5% agarose. Forty eight hours after infection, infected monolayers were fixed and stained with crystal violet to determine plaque numbers.

Synthetic peptides corresponding to the FIR domains of the MHV or SARS CoV S protein were tested for their ability to inhibit infection by these coronaviruses. The ability to inhibit formation of plaques in cell monolayers is the most stringent in vitro test of a potential infection inhibitor drug. Two peptides (GNHILSLVQNAPYGLYFI-HFSW, SEQ ID NO: 22 and GYFVQDDGEWK-FTGSSYYY, SEQ ID NO: 23) from the MHV FIR can inhibit plaque formation by MHV, though the first MHV FIR peptide is more efficient (see FIG. 8A). Two peptides from the FIR of SARS, CoV (GYHLMSFPQAAPHGVVFL-HVTY, SEQ ID NO: 24 and GVFVFNGTSWFITQRNFFS, SEQ ID NO: 25) inhibited plaque formation by this coronavirus (see FIG. 8B). There was also a significant reduction (~50%) in the average diameter of the residual plaques. These results suggest that this peptide inhibits both entry and spread of MHV. Similar results with these inhibitory peptides were obtained in independent experiments, with 50% plaque inhibition observed at concentrations of <5 µM. These results are unlikely to be explained by non-specific cytotoxic effects of the peptides. Except for the plaques, cells in the monolayers were intact and viable. The low number of plaques grew were similar in size to control plaques. Peptides from other regions also inhibited infection by these viruses, but to a lesser extent than the most active FIR peptides (FIG. 8). For example, peptides from the fusion peptide region and the carboxyl terminal helix (C-helix) of the MHV S and SARS CoV S provided some inhibition (MHV S fusion peptide=MFPPWSAAAGVPFSLSVQY, SEQ ID NO: 26; MHV S C-helix= QDAIKKLNESYIN-LKEVGTYEMYVKW, SEQ ID NO: 27; SARS CoV S fusion peptide=MYKTPTLKYFGGFNFSQIL, SEQ ID NO: 28; SARS CoV S C-helix= AACEVAKNLNESLIDLQEL-GKYEQYIKW, SEQ ID NO: 29 Inhibitory activities in the, mM range were recently reported with coronavirus C-helix peptides by Bosch et al., (2003) and others (Bosch et al., 2004; Lui et al., 2004; Yuan et al., 2004; Zhu et al., 2004). However, no FIR coronavirus inhibitory peptides have been reported. Nevertheless, in view of the current invention, the cited references collectively, provide support for the tremendous advantages of the currently disclosed and claimed inventions. That is, these references are consistent with the inventors' assertion that the methods of the present invention can be advantageously used to identify synthetic peptides that inhibit fusion/infectivity by members of the Coronaviridae family.

Example 4: Identification of Arenavirus Fusion Inhibitory Peptides. Background

Lassa fever is an often-fatal hemorrhagic illness named for the town in the Yedseram River valley of Nigeria in which the first described cases occurred in 1969 (Buckley and Casals, 1970). Parts of Guinea, Sierra Leone, Nigeria, and Liberia are endemic for the etiologic agent, Lassa virus (LasV). The public health impact of LasV in endemic areas is immense. The Centers for Disease Control, and Prevention (CDC) have estimated that there are 100,000-300,000 cases of Lassa per year in West Africa and 5,000 deaths. In some parts of Sierra Leone, 10-15% of all patients admitted to hospitals have Lassa fever. Case fatality rates for Lassa fever are typically 15% to 20%, although in epidemics overall mortality can be as high as 45%. The mortality rate for women in the last month of pregnancy is always high, about 90%, and LasV infection causes high rates of fetal death at all stages of gestation. Mortality rates for Lassa appear to be higher in non-Africans, which is of concern because Lassa is the most commonly exported hemorrhagic fever. Because of the high case fatality rate and the ability to spread easily by human-human contact, LasV is classified as a Biosafety Level 4 and NIAID Biodefense category A agent.

LasV is a member of the Arenaviridae family. The genome of arenaviruses consists of two segments of single-stranded, ambisense RNA. When viewed by transmission electron microscopy, the enveloped spherical virions (diameter: 110-130 nm) show grainy particles that are ribosomes acquired from the host cells (Murphy and Whitfield, 1975). Hence, the use for the family name of the Latin "arena", which means "sandy". In addition to LasV, other arenaviruses that cause illness in humans include Junin virus (Argentine hemorrhagic fever), Machupo virus (Bolivian hemorrhagic fever), Guanarito virus (Venezuelan hemorrhagic fever) and Sabia virus (Brazilian hemorrhagic fever). Arenaviruses are zoonotic; each virus is associated with a specific species of rodent (Bowen, Peters, and Nichol, 1997). The reservoir of LasV is the "multimammate rat" of the genus *Mastomys* (Monath et al., 1974). The wide distribution of *Mastomys* in Africa makes eradication of this rodent reservoir impractical and ecologically undesirable.

Signs and symptoms of Lassa fever, which occur 1-3 weeks after virus exposure, are highly variable, but can include fever, retrosternal, back or abdominal pain, sore throat, cough, vomiting, diarrhea, conjunctival injection, and facial swelling. LasV infects endothelial cells, resulting in increased capillary permeability, diminished effective circulating volume, shock, and multi-organ system failure. Frank bleeding, usual mucosal (gums, etc.), occurs in less than a third of cases, but confers a poor prognosis. Neurological problems have also been described, including hearing loss, tremors, and encephalitis. Patients who survive begin to defervesce 2-3 weeks after onset of the disease. The most common complication of Lassa fever is deafness. Temporary or permanent unilateral or bilateral deafness occurs in approximately 30% of Lassa fever patients during convalescence, and is not associated with the severity of the acute disease. The antiviral drug ribavirin is effective in the treatment of Lassa fever, but only if administered early (up to six days) in the course of illness (Johnson et al., 1987; McCormick et al., 1986). It is unknown whether ribavirin is effective against other arenaviruses, such as Junin, Machupo, Guanarito or Sabia viruses. No LasV vaccine is currently available.

Materials And Methods.

Vero cells were maintained as monolayers in Basal Medium Eagle (BME) containing 10 mM HEPES and 5% FBS. Lassa virus (Josiah strain) was propagated on Vero cells. For plaque assays, Vero cells were seeded at a density of $1 \times 10^6$ cells in each well of a 6-well plate. Fifty to 100 p. f. u. of LasV were pre-incubated with or without peptide in serum-free BME for 1 hour. Cells were then infected with peptide-treated inoculum or vehicle control inoculum. After 1 hour adsorption, the inoculum was removed, cells were washed twice with 1× phosphate buffered saline, and the cells were overlaid with 2 ml of 0.5% agarose in BME containing 10 mM HEPES and 5% FBS, and incubated for 4 days. A second overlay containing 5% neutral red was applied, and plaques were counted 24 hours later.

Results And Discussion.

Figure 9:
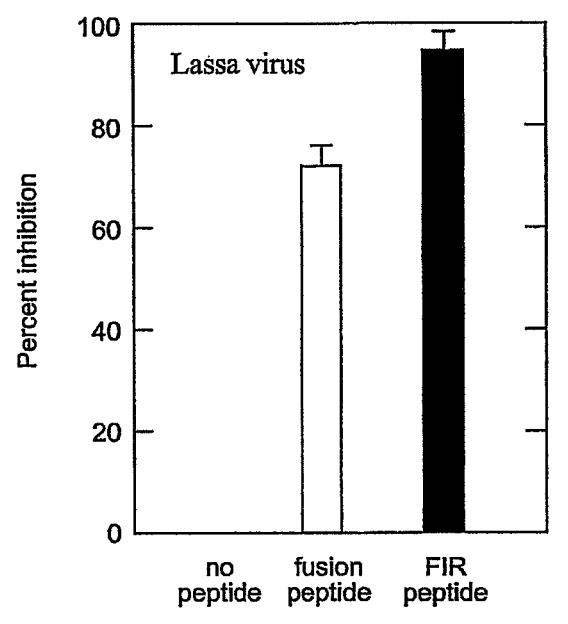

Synthetic peptides corresponding to the FIR domains of LasV glycoprotein 2 (GP2) were tested for their ability to inhibit infection by this arenavirus. A peptide (NYSKY-WYLNHTTTGR, SEQ ID NO: 30) analogous to the sequence NYSRYWYLNHTSTGK from SEQ ID NO: 1 (LASSA FIR) can inhibit plaque formation by LasV (FIG. 9). A peptide analogous to another GP2 region, the fusion peptide, (GTFTWTLSDSEGKDTPGGY, SEQ ID NO: 31) also inhibited infection by LasV, but to a lesser extent (FIG. 9). No arenavirus inhibitory peptides have been reported. Collectively, these results suggest that our approaches can identify synthetic peptides that inhibit fusion/infectivity by members of the Arenaviridae. These results, in combination with our results with coronavirus FIR inhibitory peptides, establish proof of the principle that FIR regions peptides can function as viral inhibitors Each of the following documents is herein incorporated by reference:

Bolognesi et al. U.S. Pat. No. 5,464,933;
Bosch et al. *Proc Natl Acad Sci USA* 101: 8455-8460;
Bosch et al. *J Virol* 77: 8801-8811;
Bowen et al. (1997) *Mol Phylogen Evol* 8 (3), 301-16;
Buckley (1970) *Am J Trop Med Hyg* 19 (4), 680-91;
Can et al. (1993) *Cell* 73 (4), 823-32;
Chan et al. *Cell* 89 (2), 263-73;
Chen et al. *Structure* 9 (3), 255-266;
Clark-Lewis et al. *Science* 231: 134-9;
Drosten et al. *New England J Med* 348, 1967-76;
Gallaher et al. *Adv. Membrane Fluidity* 6, 113-142;
Gallaher (1987) *Cell* 50 (3), 327-8;
Gallaher (1996) *Cell* 85, 1-2;

Gallaher et al. *AIDS Res Human Retroviruses* 5 (4), 431-40;
Gallaher et al. *BMC Microbiol* 1 (1), 1;
Gallaher et al., www(dot)virology(dot)net/Articles/sars/s2model.html; May 1, 2003;
Gonzalez-Scarano et al. (1987) *AIDS Res Hum Retroviruses* 3 (3) 245-52;
Guan et al. (2004) *Lancet* 363, 99-104;
Guan et al. (2003) *Science* 302, 276-278;
Henderson et al. U.S. Pat. No. 5,567,805;
Jaysinghe et al. (2000) www(dot)blanco(dot)biomol(dot)uci(dot)edu/index;
Johnson et al. *J Infect Dis* 155 (3), 456-64;
Kilby et al. (1998) *Nat Med* 4 (11), 1302-7;
Kowalski et al. (1991) *J Virol* 65, 281-291;
Ksiazek et al. (2003) *N Engl J Med* 348, 1953-66;
Lambert et al. (1996) *Proc Natl Acad Sci USA* 93 (5), 2186-91;
Liu et al. (2004) *Lancet* 363: 938-947;
Malashkevich et al. (1999) *Proc Natl Acad Sci USA* 96 (6), 2662-7;
Marra et al. (2003) *Science* 300, 1399-1404;
McCormick et al. (1986) *N Engl J Med* 314 (1), 20-6;
Monath et al. (1974) *Science* 185 (147), 263-5;
Murphy et al. (1975) *Bull World Health Organ* 52 (4-6), 409-19;
Owens et al. (1990) *AIDS Res Hum Retroviruses* 6 (11), 1289-96;
Peiris et al. (2003) *Lancet* 361, 1319-25;
Pozniak (2001) *JHIV Ther* 6 (4), 91-4;
Poutanen et al. (2003) *New England J Med* 348, 1995-2005;
Qureshi et al. (1990) *AIDS* 4, 553-558;
Richardson et al. (1980) *Virology* 105 (1), 205-22;
Rota et al. (2003) *Science* 300, 1394-1399;
Silburn et al. (1998) *AIDS Res Hum Retroviruses* 14 (5), 385-92;
Sodroski et al. (1999) *Cell* 99 (3), 243-6;
Suarez et al. (2000) *J Virol* 74 (17), 8038-47;
Watanabe et al. (2000) *J Virol* 74 (21), 10194-201;
Weissenhom et al. (1998) *Mol Cell* 2 (5), 605-16;
Weissenhom et al. (1997) *Nature* 387 (6631), 426-30;
Wild et al. (1993) *Human Retroviruses* 9 (11), 1051-3;
Wild et al. (1992) *Proc Natl Acad Sci USA* 89 (21), 10537-41;
Wilson et al. (1981) *Nature* 289 (5796), 366-73;
Young et al. (1999) *J Virol* 73 (7), 5945-56;
Yuan et al. (2004) *Biochem Biophys Res Commun* 319: 746-752; and
Zhu et al. (2004) *Biochem Biophys Res Commun* 319: 283-288.

What is claimed is:

1. A pharmaceutical composition for treating an ongoing measles virus infection by inhibiting fusion of the virus with a host cell membrane, the composition comprising a polypeptide in a sterile biocompatible pharmaceutical carrier; wherein the polypeptide consists of SEQ ID NO: 5 or SEQ ID NO. 6.

2. The composition of claim 1, wherein the polypeptide includes a macromolecular carrier at the amino-terminus thereof, wherein the macromolecular carrier is selected from the group consisting of a lipid conjugate, a polyethylene glycol moiety, and a carbohydrate moiety.

3. The composition of claim 1, wherein the sterile biocompatible pharmaceutical carrier further comprises a penetrant.

4. The composition of claim 1, wherein the sterile biocompatible pharmaceutical carrier comprises a buffered saline solution.

5. The composition of claim 1, wherein the polypeptide consists of SEQ ID NO: 5.

6. The composition of claim 1, wherein the polypeptide consists of SEQ ID NO: 6.

7. A method for treating an ongoing measles virus infection by inhibiting fusion of the virus with a host cell membrane, the method comprising:

administering to a subject suffering from a measles infection a composition of claim 1.

8. The method of claim 7, wherein the polypeptide of the composition includes a macromolecular carrier at the amino-terminus thereof, wherein the macromolecular carrier is selected from the group consisting of a lipid conjugate, a polyethylene glycol moiety, and a carbohydrate moiety.

9. The method of claim 7, wherein the sterile biocompatible pharmaceutical carrier of the composition further comprises a penetrant.

10. The method of claim 7, wherein the sterile biocompatible pharmaceutical carrier of the composition comprises a buffered saline solution.

11. The method of claim 7, wherein the administering step comprises intranasally administering the composition.

12. The method of claim 7, wherein the polypeptide of the composition consists of SEQ ID NO: 5.

13. The method of claim 7, wherein the polypeptide of the composition consists of SEQ ID NO: 6.

* * * * *